(12) United States Patent
Guy et al.

(10) Patent No.: US 12,263,947 B2
(45) Date of Patent: Apr. 1, 2025

(54) INTELLIGENT SETTINGS OF AN AIRCRAFT PASSENGER SUITE

(71) Applicant: Safran Seats GB Limited, Cwmbran (GB)

(72) Inventors: Julian Guy, Cwmbran (GB); Rachel James, Cwmbran (GB); Huang-Yu Teh, Cwmbran (GB)

(73) Assignee: Safran Seats GB Limited, Cwmbran (GB)

( * ) Notice: Subject to any disclaimer, the term of this patent is extended or adjusted under 35 U.S.C. 154(b) by 344 days.

(21) Appl. No.: 17/785,892

(22) PCT Filed: Dec. 15, 2020

(86) PCT No.: PCT/GB2020/053214
§ 371 (c)(1),
(2) Date: Jun. 15, 2022

(87) PCT Pub. No.: WO2021/123749
PCT Pub. Date: Jun. 24, 2021

(65) Prior Publication Data
US 2023/0024865 A1  Jan. 26, 2023

(30) Foreign Application Priority Data

Dec. 16, 2019  (GB) ..................................... 1918524

(51) Int. Cl.
*H04L 12/28* (2006.01)
*B64D 11/06* (2006.01)
*A61B 5/00* (2006.01)

(52) U.S. Cl.
CPC ...... *B64D 11/0606* (2014.12); *B64D 11/0602* (2014.12); *B64D 11/0626* (2014.12);
(Continued)

(58) Field of Classification Search
CPC .................................................. H04L 12/2816
See application file for complete search history.

(56) References Cited

U.S. PATENT DOCUMENTS 10,144,512 B2  12/2018  Gagnon et al.
2013/0338857 A1  12/2013  Sampigethaya
(Continued)

FOREIGN PATENT DOCUMENTS

CN  104859489 A  8/2015
CN  110891860 A  * 3/2020 ............. B64D 11/00
(Continued)

OTHER PUBLICATIONS

China Patent Application 201980043327.8, Office Action, dated Apr. 14, 2023.
(Continued)

*Primary Examiner* — Suresh Suryawanshi
(74) *Attorney, Agent, or Firm* — Kilpatrick Townsend & Stockton LLP

(57) ABSTRACT

An aircraft passenger suite is provided. The suite comprises an aircraft seat for use by a passenger. The suite also comprises a controller for controlling a number of output states of the suite, the controller comprising a logic condition receiver operable to receive a logic condition input. The suite also comprises sensor equipment operable to provide a sensor input to the controller, the sensor input providing an indication of at least one attribute of a passenger of the suite. The sensor equipment comprises one or more of: an image sensor a pressure sensor and a physiological sensor. The controller is configured to control at least one of the output states of the suite based on both the logic condition input and the sensor input.

17 Claims, 21 Drawing Sheets

(52) U.S. Cl.
CPC ......... *A61B 5/6888* (2013.01); *H04L 12/2816* (2013.01); *Y04S 20/20* (2013.01)

(56) References Cited

U.S. PATENT DOCUMENTS

| | | |
|---|---|---|
| 2018/0140798 A1 | 5/2018 | Tomiyama et al. |
| 2018/0170550 A1* | 6/2018 | Streckert ............ B64D 11/0015 |
| 2018/0181919 A1 | 6/2018 | Jobling et al. |
| 2018/0281673 A1 | 10/2018 | Garing et al. |
| 2020/0184239 A1* | 6/2020 | Skelly ..................... G06F 3/005 |
| 2021/0031924 A1* | 2/2021 | Dowty ..................... B60Q 3/00 |

FOREIGN PATENT DOCUMENTS

| | | | |
|---|---|---|---|
| EP | 2910471 A1 | 8/2015 | |
| EP | 3141482 A1 | 3/2017 | |
| EP | 3521166 A1 | 8/2019 | |
| EP | 3439959 B1 * | 8/2021 | ......... B64D 11/0638 |
| GB | 2575058 A * | 1/2020 | ............. B64D 11/00 |
| WO | 2016191560 A1 | 12/2016 | |

OTHER PUBLICATIONS

China Patent Application 201980043327.8, Search Report, dated Apr. 7, 2023.
International Patent Application No. PCT/GB2020/053214, International Search Report and Written Opinion, dated Mar. 9, 2021.
United Kingdom Patent Application No. 1918524.8, Search Report, dated Sep. 25, 2020.

* cited by examiner

INTELLIGENT SETTINGS OF AN AIRCRAFT PASSENGER SUITE

CROSS REFERENCE TO RELATED APPLICATION

This application is a national phase application of International Patent Application PCT/GB2020/053214, filed on Dec. 15, 2020 and titled "An Aircraft Passenger Suite," which is related to and claims priority to United Kingdom Patent Application No. 1918524.8, filed on Dec. 16, 2019, both of which are hereby incorporated by reference in their entireties.

BACKGROUND OF THE INVENTION

The present disclosure relates to aircraft passenger suites.

The present invention concerns an aircraft passenger suite. More particularly, but not exclusively, this invention concerns an aircraft passenger suite comprising an aircraft seat for use by a passenger, the aircraft passenger suite also comprising a controller, for controlling a number of output states of the aircraft passenger suite, the controller having a logic condition receiver for receiving a logic condition input.

The invention also concerns a method of controlling output states of an aircraft passenger suite.

WO 2016/191560 discloses an aircraft lighting system that is adjustable based on a location of, for example, a drinks trolley. For example, the lighting around a passenger seat can be activated when the drinks trolley approaches. The location of the trolley is detected using an RFID tag.

In other prior art aircraft suites, various lighting and seat settings can be varied based on a passenger activating the light/seat, for example.

However, none of these examples provide for different suite settings, based on intelligently deciding what the best seat/lighting setting etc. (e.g. suite environment), for a given scenario might be. The present invention seeks to mitigate the above-mentioned problems. Alternatively or additionally, the present invention seeks to provide an improved aircraft passenger suite.

SUMMARY OF THE INVENTION

The present invention provides, according to a first aspect, an aircraft passenger suite comprising an aircraft seat for use by a passenger, the aircraft passenger suite also comprising a controller for controlling a number of output states of the aircraft passenger suite, the controller comprising a logic condition receiver operable to receive a logic condition input. The aircraft passenger suite also comprises sensor equipment operable to provide a sensor input to the controller, the sensor input providing an indication of at least one attribute of a passenger of the aircraft passenger suite, the sensor equipment comprising one or more of: an image sensor, a pressure sensor and a physiological sensor. The controller is configured to control at least one of the output states of the aircraft passenger suite based on both the logic condition input and the sensor input.

Providing sensor equipment enables one or more passenger attributes to be determined and used, along with a logic condition input, to control an output state of the suite. Examples of such passenger attributes include, but are not limited to, a breathing rate, a heart rate, and a body temperature of the passenger. Other examples of such passenger attributes include, but are not limited to, a posture, a comfort characteristic, a presence, a location, and a movement of the passenger. The controller can control the output state based on the received logic condition and the received sensor input. That output state may be pre-decided, based on the logic condition and the sensor input scenario. This allows the output state(s) of the suite to be controlled in a more intelligent, flexible and/or versatile manner, compared to known systems.

Preferably, the output state controllable by the controller controls an environment within the aircraft passenger suite. Hence, the controller is configured to control the environment of the aircraft passenger suite based on the logic condition input and the sensor input. Controlling the environment of the aircraft passenger suite may provide a more pleasant, comfortable and/or convenient experience for the passenger.

In some examples, the sensor equipment comprises an image sensor. The image sensor may obtain image data representing all or part of the suite (e.g. the interior of the suite). The image data may be processed to determine one or more passenger attributes. Preferably, processing the image data comprises performing image data analysis. Image data analysis may involve performing object detection and/or object recognition on the image data. Such image data analysis may be performed at the controller and/or at the sensor equipment. The image data may be analysed to determine a presence, position, posture and/or movement of the passenger or a part of the passenger.

Preferably, the image sensor comprises or is comprised in a thermal imaging equipment arranged to obtain a thermal image of at least part of the aircraft passenger suite. The thermal imaging equipment may be configured to obtain the thermal image based on infrared radiation received at the image sensor. As such, the image sensor may comprise an infrared sensor. Thermal imaging may be preferable to other types of imaging as it provides greater anonymity and/or privacy for the passenger. Moreover, performing object detection and/or recognition using thermal image data may be more reliable and/or efficient than performing object detection and/or recognition using other types of image data. This is particularly the case when the objects to be detected and/or recognised are parts of a passenger, which are warmer than surrounding objects and are therefore readily detectable in a thermal image. Thermal image data may have a lower image resolution than other types of image data, thereby increasing processing efficiency. Further, thermal image data may be analysed to determine a body temperature of the passenger. For example, the body temperature of the passenger may be determined based on an obtained thermal image of the forehead of the passenger.

Additionally or alternatively, the image sensor may comprise or be comprised in an imaging equipment arranged to obtain an image of at least part of the aircraft passenger suite based on visible light received at the image sensor. As such, the image sensor may comprise a visible light sensor. In some examples, the image sensor comprises or is comprised in a video equipment (e.g. a video camera).

Preferably, the sensor equipment comprises a plurality of image sensors, each of the plurality of image sensors being arranged in a different location in the aircraft passenger suite, wherein the controller is configured to obtain data representing a three-dimensional map of a volume within the aircraft passenger suite, the data generated using sensor input provided by the plurality of image sensors. Providing a three-dimensional map of a volume within the suite enables a more accurate and/or reliable detection of the position of the passenger than a case in which such a three-dimensional map is not provided. For example, such a three-dimensional map (e.g. obtained using thermal imaging) may be used to determine whether or not a body part of the passenger is in a deployment/stowage path of a furniture item of the suite. Preferably, the plurality of image sensors comprises a plurality of infrared sensors, arranged to obtain a three-dimensional thermal map of a volume within the suite. The three-dimensional thermal map may be processed to determine passenger attributes such as body temperature, position, posture, etc.

In some examples, the sensor equipment comprises a pressure sensor, wherein the pressure sensor is arranged under a support surface of the aircraft seat. Such a pressure sensor may be used to determine whether or not the passenger is seated, and/or to determine a position of the passenger in the seat. The pressure sensor may be configured to provide pressure sensor data to the controller.

The aircraft seat may comprise a first seat part and a second seat part moveable with respect to the first seat part, the first seat part and the second seat part each comprising a respective support surface. Preferably, the sensor equipment comprises a first pressure sensor arranged under the support surface of the first seat part and a second pressure sensor arranged under the support surface of the second seat part. For example, the first pressure sensor may be arranged in a seat pan and the second pressure sensor may be arranged in a backrest or armrest. As such, a plurality of pressure sensors may be distributed under support surfaces of different seat parts. Such an arrangement may be used to determine a position and/or posture of the passenger, and/or whether or not the passenger is moving. For example, pressure sensors may be used to determine whether a passenger is sitting in a seat, lying in a bed, sitting upright in the bed, and/or sitting in the seat with another passenger sitting on an ottoman.

In some examples, the sensor equipment comprises a physiological sensor. A physiological sensor is a sensor that is operable to measure and/or obtain one or more physiological characteristics of the passenger. The physiological characteristics may comprise medical-related characteristics. The physiological sensor may be configured to provide physiological sensor data to the controller. Preferably, the physiological sensor comprises one or more of: a heart rate sensor, a breathing rate sensor and/or a body temperature sensor. As such, the physiological sensor may be operable to measure and/or obtain a heart rate, a breathing rate and/or a body temperature of a passenger. Preferably, the physiological sensor comprises a contactless sensor. Alternatively, the physiological sensor may be arrangeable to be in contact with the passenger. A heart rate sensor may be configured to send light into the skin of the passenger and measure the amount of light that is reflected. A body temperature sensor may comprise a thermal image sensor, or may comprise a temperature sensor arrangeable to be in the aircraft seat or worn by the passenger. A breathing rate sensor may be configured to obtain image or video data and analyse such data to track breathing motion. Additionally or alternatively, the breathing rate sensor may comprise a microphone and/or a motion sensor.

The sensor equipment may of course comprise any combination of image sensors, pressure sensors and/or physiological sensors. For example, the controller may control at least one of the output states of the aircraft passenger suite based upon a logic condition input and sensor input obtained from more than one different type of sensor.

In some examples, the at least one attribute of the passenger comprises one or more of: a breathing rate, a heart rate, and a body temperature of the passenger. Therefore, the at least one attribute may comprise a physiological attribute of the passenger.

In some examples, the at least one attribute of the passenger comprises one or more of: a posture, a comfort characteristic, a presence, a location, and a movement of the passenger. Hence, the controller is able to determine a number of physical and/or physiological characteristics of the passenger at a given point in time, and control output states of the suite accordingly.

Preferably, the logic condition input includes an aircraft state, an aircraft cabin state, an aircraft passenger suite state, and/or one or more preferences provided by the passenger.

The logic condition input may include an aircraft state, wherein the aircraft state represents a status of the aircraft, such as: "boarding", "ready for taxi, take-off or landing (TTL)", "in flight", "experiencing turbulence", "landed" and/or "lifejacket inspection check".

The logic condition input may include an aircraft cabin state, wherein the aircraft cabin state represents a status of the aircraft cabin, such as: "lights dimmed for night-time" and/or "meal time".

The logic condition input may include an aircraft passenger suite state, wherein the aircraft passenger suite state represents a status of the aircraft passenger suite, such as: "seat in bed configuration", "lights low/off", "furniture being deployed" "furniture being stowed", "furniture stowed" and/or "furniture deployed".

The logic condition input may include one or more preferences provided by the passenger. Preferably, the one or more preferences includes an indication of passenger consent. Hence, the controller may be configured to control the output states of the suite on the condition of passenger consent and/or other preferences of the passenger. In some examples, the passenger attributes are determined on the condition of passenger consent and/or other preferences of the passenger. The preferences may be provided via a personal electronic device of the passenger, or via a user interface of the controller. In some cases, passenger consent is provided by connecting the personal electronic device to the controller or another device of the suite, and by allowing data to be communicated from the personal electronic device to the controller or other suite device.

Of course, the logic condition input may include a combination of states and/or preferences. For example, the controller may control at least one of the output states of the aircraft passenger suite based upon a logic condition input, that is dependent on more than one state and/or user preference, and the sensor input.

Preferably, the output state controllable by the controller helps provide a desired or required aircraft passenger suite environment. The output state may include at least one of: a light level of the aircraft passenger suite, a temperature of the passenger aircraft suite or a part of the aircraft passenger suite, a message or warning displayed within the aircraft passenger suite, and/or a deployment/stowage condition of a piece of furniture of the aircraft passenger suite. In some examples, the output state controllable by the controller includes a message or warning displayed externally to the aircraft passenger suite, such as a message or warning displayed to a member of crew.

In some examples, the output state controllable by the controller includes providing an indication of whether or not medical assistance is required. Such an indication may be provided to the crew and/or to medical support on the ground. In some examples, the output state controllable by the controller includes controlling a display device of the aircraft passenger suite to aid passenger comfort. Hence, the controller can help in providing assistance to a passenger suffering from discomfort, anxiety and/or a medical problem.

In some examples, the sensor equipment comprises an image sensor, the logic condition input includes an aircraft state, and the output state controllable by the controller is a message display within the suite and/or a lighting level within the suite, such that, in use, if the sensor input indicates that a passenger has entered the suite, and the aircraft state is "boarding", then the controller controls the output state such that a welcoming message is displayed and/or welcome lighting is turned on. The image sensor obtains image data that is useable (e.g. by the controller) to detect the presence of a body within the suite. A greeting may be displayed on a display monitor of the suite. The welcome lighting may help the passenger to identify various features and/or furniture items of the suite. In some examples, one or more pressure sensors (e.g. arranged under a support surface of the seat) may be used to determine that the passenger has entered the suite, thereby to trigger the welcome mode. Other types of sensor (e.g. a door sensor configured to detect opening and/or closing of a suite door) may additionally or alternatively be used to provide an indication that the passenger has entered the suite.

In some examples, the sensor equipment comprises an image sensor and/or a pressure sensor, the logic condition input includes an aircraft state, and the output state controllable by the controller is a message/warning light within the suite and/or externally to a member of cabin crew, such that, in use, if the sensor input indicates that a passenger is not seated in the aircraft seat, and the aircraft state is "ready for TTL", then the controller controls the output state such that the message/warning light is turned on. The output state making the passenger and/or cabin crew aware (i.e. the message/warning light) may turn off when the passenger sits in the seat. The passenger sitting in the seat may be detected by the image sensor and/or the pressure sensor. In some examples, the sensor input indicates whether or not the passenger is wearing a seatbelt, whether the seat is positioned correctly for TTL, and/or whether luggage and/or furniture is stowed correctly for TTL.

In some examples, the sensor equipment comprises an image sensor and/or a pressure sensor, the logic condition input includes an aircraft cabin state and/or an aircraft suite state, and the output state controllable is a lighting level within the suite, such that, in use, if the sensor input indicates that a passenger has got out of bed, and the aircraft cabin state is "lights dimmed for night-time" and/or the aircraft suite state is "low light level", then the controller controls the output state such that a light is turned on within the suite. Preferably, the light turned on is at floor level. For example, the light may comprise a light strip of relatively low intensity light near the floor of the suite. This helps the passenger to see as they move around the suite. As such, the suite may be kept dark to facilitate passenger sleep, but the risk of tripping or colliding with furniture when the passenger gets out of bed is reduced. The light may be turned off when the passenger returns to bed.

In some examples, the sensor equipment comprises an image sensor and/or a pressure sensor, the logic condition input includes an aircraft suite state, and the output state controllable is deployment/stowage of a piece of furniture, such that, in use, if the sensor input indicates that a passenger or part of the passenger is in the path of deployment/stowage, and the aircraft suite state is "deployment/stowage of a piece of furniture", then the controller controls the output state such that deployment/stowage movement of the piece of furniture is ceased. This allows deployment/stowage of the furniture item (e.g. a seat or table) to be made more safe and/or reliable, by preventing objects (including parts of the passenger) becoming trapped or stuck. In some cases, this allows the deployment/stowage to be controlled by a one touch process (i.e. a passenger touches a button once and deployment/stowage is initiated and continues until complete or until an object in the deployment/stowage path is detected) whilst still being safe and preventing objects getting stuck. The deployment/stowage movement of the piece of furniture may be resumed if/when the passenger or part of the passenger is no longer in the path of deployment/stowage.

In some examples, the sensor equipment comprises an image sensor and/or a pressure sensor, the logic condition input includes an aircraft suite state and/or an aircraft cabin state, and the output state controllable is deployment/stowage of the meal table, such that, in use, if the sensor input indicates that a passenger is sitting in the seat, and the aircraft suite state is "deployment/stowage of the meal table" and/or the aircraft cabin state is "meal time", and the meal table is stowed, then the controller controls the output state such that the meal table is deployed. In some examples, the controller is configured to adjust the lighting within the suite, e.g. to change from a "work mode" to a "dining mode". A working environment may benefit from a brighter suite illumination, whereas a dining environment may benefit from softer lighting, preferably focused on the meal table. Preferably, the deployed meal table is moveable. For example, the meal table may be able to translate on a plane that is substantially parallel to the plane of the table (e.g. towards and away from the seat). In such cases, the position of the meal table may be detected using the sensor equipment, and the controller may adjust the focus position of a light within the suite such that the meal table remains illuminated. In some examples, the position of the passenger is detected (e.g. using the image sensor and/or pressure sensor), and the controller moves the meal table according to the position of the passenger. Preferably, the sensor equipment is also configured to detect whether any obstacles are present in the path of table movement. If any obstacles are detected, movement of the table may be ceased.

In some examples, the aircraft passenger suite is configurable to allow two (or more) passengers to dine together. In this case, if the sensor input indicates that two passengers are sitting in the suite, and the aircraft cabin state is "meal time", and the meal table is deployed, then the controller controls the output state such that the meal table is moved according to the positions of the passengers. The positions of the passengers may be detected using the image sensor and/or pressure sensor.

In some examples, a pressure sensor is arranged at an edge of a support surface. Preferably, the pressure sensor is arranged at an edge of the seat pan that is furthest from the backrest. When the seat is moved to a bed configuration, such an edge may meet (i.e. become contiguous with) another edge, such as a near edge of an ottoman or leg rest. Hence, the pressure sensor can detect whether any objects, including parts of the passenger, are likely to become trapped when the seat is moved to the bed configuration. Movement of the seat to the bed configuration may be prevented accordingly, and/or a message/warning light may be turned on. In some cases, this allows the movement of the seat to be controlled by a one touch process (i.e. a passenger touches a button once and seat movement is initiated and continues until complete or until an object in the seat path is detected) whilst still being safe and preventing objects getting stuck. The movement of the seat may be resumed if/when the passenger or part of the passenger is no longer in the seat path.

In some examples, the sensor equipment comprises a physiological sensor, the logic condition input includes one or more preferences provided by a passenger, and the output state controllable is providing an indication of whether or not medical assistance is required, such that, in use, if the sensor input indicates that a passenger requires medical assistance, and the one or more preferences indicate that the passenger has provided consent, then the controller controls the output state such that an indication that medical assistance is required is provided. Preferably, the body temperature, breathing rate and/or heart rate of the passenger are measured. The body temperature may be determined using a thermal camera, for example. The breathing rate may be determined using a camera and/or microphone. The heart rate may be determined using a heart rate sensor built into the aircraft seat. If one or more of these sensors detects an unexpected and/or extreme value, the crew can be alerted to assist the passenger.

Preferably, the medical information collected is stored and transmitted to medical support on the ground if a medical emergency develops. In some cases, passengers can track pre-existing medical conditions (e.g. blood pressure or blood sugar levels) using a personal electronic device, and this information may then be made available to the crew and/or to medical support on the ground. For example, the personal electronic device may send such medical information to the controller of the aircraft suite, which in turn sends the information to the crew and/or medical support if a medical emergency develops.

In some examples, the sensor equipment comprises a physiological sensor, the logic condition input includes one or more preferences provided by a passenger, and the output state controllable is a lighting or cooling condition within the suite, such that, in use, if the sensor input indicates that a passenger is anxious, and the one or more preferences indicate that passenger has provided consent, then the controller controls the output state such that cooling and/or air circulation is turned on, suite lighting is adjusted, and/or a display device of the suite is controlled to aid passenger comfort. Anxiety may be detected based on the measured breathing rate, heart rate and/or body temperature of the passenger being different than expected.

In some examples, the sensor equipment comprises a physiological sensor, the logic condition input includes one or more preferences provided by a passenger, and the output state controllable is a heating or cooling condition within the suite, such as heating or cooling of the aircraft seat, such that, in use, if the sensor input indicates that a passenger is hotter or colder than expected, and the one or more preferences indicate that the passenger has provided consent, then the controller controls the output state such that heating, cooling, air circulation and/or air conditioning in the aircraft suite is turned on. This helps to make the passenger more comfortable. Preferably, the physiological sensor comprises a body temperature sensor. The body temperature sensor may comprise or be comprised in a thermal imaging equipment. The heating, cooling, air circulation and/or air conditioning may be turned off when the body temperature of the passenger returns to an expected level.

In some examples, the sensor equipment comprises a breathing rate sensor, the logic condition input includes an aircraft suite state and/or one more preferences provided by a passenger, and the output state controllable is a lighting level and/or noise cancellation within the suite, such that, in use, if the sensor input indicates that a passenger is asleep, and the aircraft suite state is "seat in bed configuration" and/or the one or more preferences indicate that the passenger has provided consent, then the controller controls the output state such that a lighting level within the suite is adjusted and/or noise cancellation is turned on. This can help the passenger to sleep and/or make the passenger more comfortable. Preferably, the logic condition input includes a destination time zone and/or an estimated landing time, and the lighting level within the suite is adjusted based on the destination time zone and/or estimated landing time. This can help the passenger to adjust to the destination time zone, and/or reduce the effects of jet lag.

The sensor equipment may further comprise a distance measurement equipment for measuring a distance between a first location within the suite and a second location within the suite and providing a distance input to the controller, wherein, in use, the controller controls the at least one output state based on the distance input. Preferably, the distance measurement equipment comprises a signal emitter for a emitting a signal at a first time, and a signal receiver, for receiving the signal at a second time, a time lag between the first and second times corresponding to the distance being measured. Hence the time lag (elapsed time) is an indication of the distance and can be used to provide the distance input. The signal emitter may emit an infrared or an ultrasound signal, for example. The signal receiver is suitable for receiving the signal emitted by the signal receiver.

In some examples, the signal emitter and signal receiver are located substantially adjacent each other at the first location. In such examples, an object at the second location reflects the signal emitted from the signal emitter back to the signal receiver. In other examples, the signal emitter and signal receiver are located at substantially different locations within the suite. For example, the signal emitter may be located at the first location and the signal receiver may be located at the second location. The signal emitter and/or the signal receiver may be fixedly mounted to a piece of furniture within the aircraft suite. This may correspond to the first location. The second location within the suite preferably corresponds to the location of a moveable object, such as a passenger or a piece of luggage.

According to a second aspect of the present invention, there is provided a method of controlling a number of output states of an aircraft passenger suite, the aircraft passenger suite comprising an aircraft seat for use by a passenger. The method comprises: receiving a logic condition input; receiving a sensor input from sensor equipment, the sensor equipment comprising one or more of an image sensor, a pressure sensor and a physiological sensor; determining, using the sensor input, at least one attribute of a passenger of the aircraft passenger suite; and controlling a number of output states of the aircraft passenger suite, based on both the logic condition input and the at least one attribute.

According to a third aspect of the present invention, there is provided an aircraft passenger suite comprising an aircraft seat for use by a passenger, the aircraft passenger suite also comprising a controller for controlling a number of output states of the aircraft passenger suite, the controller comprising a first receiver operable to receive a logic condition input, and a second receiver operable to receive image, pressure and/or physiological sensor data from sensor equipment, the sensor data providing an indication of one or more attributes of a passenger of the aircraft passenger suite, wherein the controller is configured to control at least one of the output states of the aircraft passenger suite based on both the logic condition input and the sensor data.

Preferably, the controller is communicatively coupleable to a personal electronic device of the passenger. Examples of personal electronic devices include, but are not limited to, mobile devices, tablet devices and smart watch devices. The controller is configured to receive the sensor data from the personal electronic device. Hence, one or more sensors of the personal electronic device may be used to obtain the sensor input, which is then provided to the controller of the suite. As such, in some cases, the suite is not itself required to provide sensor equipment. Preferably, the controller is configured to receive the logic condition input from the personal electronic device. The logic condition input can be, for example, one or more passenger preferences or an indication of consent. The controller may be communicatively coupleable to the personal electronic device via a wired and/or wireless connection.

According to a fourth aspect of the present invention, there is provided an aircraft passenger suite comprising an aircraft seat for use by a passenger, the aircraft passenger suite also comprising a controller for controlling a number of output states of the aircraft passenger suite, the controller comprising a logic condition receiver operable to receive a logic condition input. The aircraft passenger suite also comprises sensor equipment operable to provide a sensor input to the controller, the sensor input providing an indication of at least one attribute of a passenger of the aircraft passenger suite. The controller is configured to control at least one of the output states of the aircraft passenger suite based on both the logic condition and the sensor input, wherein the output state controllable by the controller comprises at least one of: providing an indication of whether or not medical assistance is required; and controlling a display device of the aircraft passenger suite to aid passenger comfort.

Preferably, the logic condition input includes an indication of passenger consent. As such, an opt-in or active consent feature is included in the logic control. In some cases, passenger consent is assumed unless the passenger has actively refused consent, or 'opted out'. If a passenger does not provide consent, the passenger is not monitored using the sensor equipment, in some examples. Preferably, passenger consent is provided via a personal electronic device communicatively coupled to the controller.

In some examples, the sensor equipment comprises an image sensor. Preferably, the sensor equipment comprises a physiological sensor arranged to detect a physiological condition of the passenger. More preferably, the physiological sensor comprises a breathing rate sensor, a heart rate sensor and/or a body temperature sensor.

In some examples, the physiological sensor comprises a breathing rate sensor, and the output state controllable comprises displaying a measured and/or desired breathing pattern to the passenger via the display device. Displaying a measured and/or desired breathing pattern to the passenger can help to improve passenger comfort and/or reduce anxiety. For example, displaying such a breathing pattern can help to reduce the breathing rate of the passenger. The display device may comprise an in-flight entertainment (IFE) monitor. Additionally or alternatively, the display device may comprise a feature light, wherein the output of the feature light is configured to pulsate at the measured or desired breathing rate.

In some examples, the output state controllable comprises providing an indication of whether or not medical assistance is required to a crew information panel. This helps make the crew aware that the passenger requires medical assistance.

In some examples, the controller is communicatively coupleable to a personal electronic device of the passenger, wherein the logic condition receiver is operable to receive the logic condition input from the personal electronic device. This allows the passenger to provide an indication of consent, and/or their preferences, on their personal electronic device.

According to a fifth aspect of the present invention, there is provided a method of controlling a number of output states of an aircraft passenger suite, the aircraft passenger suite comprising an aircraft seat for use by a passenger. The method comprises: receiving a logic condition input; receiving a sensor input from sensor equipment; determining, user the sensor input, at least one attribute of a passenger of the aircraft passenger suite; and controlling at least one output state of the aircraft passenger suite based on both the logic condition input and the sensor input. Controlling the at least one output state comprises at least one of: providing an indication of whether or not medical assistance is required; and controlling a display device of the aircraft passenger suite to aid passenger comfort.

According to a sixth aspect of the present invention, there is provided an aircraft passenger suite comprising an aircraft seat for use by a passenger, the aircraft passenger suite also comprising a controller for controlling a number of output states of the aircraft passenger suite, the controller comprising a first receiver operable to receive a logic condition input, and a second receiver operable to receive sensor data from sensor equipment, the sensor data providing an indication of one or more attributes of a passenger of the aircraft passenger suite. The controller is configured to control at least one of the output states of the aircraft passenger suite based on both the logic condition input and the sensor data. The output state controllable by the controller comprises at least one of: providing an indication of whether or not medical assistance is required; and controlling a display device of the aircraft passenger suite to aid passenger comfort.

According to a seventh aspect of the present invention, there is provided an aircraft passenger suite comprising an aircraft seat for use by a passenger, the aircraft passenger suite also comprising a controller for controlling a number of output states of the aircraft passenger suites, the controller comprising a logic condition receiver operable to receive a logic condition input, wherein the logic condition input includes one or more preferences provided by a passenger of the aircraft passenger suite. The aircraft passenger suite also comprises sensor equipment operable to provide a sensor input to the controller, the sensor input providing an indication of at least one attribute of the passenger. The controller is configured to control at least at least one of the output states of the aircraft passenger suite based on both the logic condition input and the sensor input. Preferably, the logic condition input includes an indication of passenger consent.

In some examples, the controller is communicatively coupleable to a personal electronic device of the passenger, wherein the logic condition receiver is operable to receive the logic condition input from the personal electronic device. Hence, the one or more preferences (e.g. including an indication of consent) may be provided via the passenger's personal electronic device.

Preferably, the sensor equipment comprises one or more of: an image sensor, a pressure sensor and a physiological sensor.

According to an eighth aspect of the present invention, there is provided a method of controlling a number of output states of an aircraft passenger suite, the aircraft passenger suite comprising an aircraft seat for use by a passenger. The method comprises: receiving a logic condition input, wherein the logic condition input includes one or more preferences provided by a passenger of the aircraft passenger suite; receiving a sensor input from sensor equipment; determining, using the sensor input, at least one attribute of a passenger of the aircraft passenger suite; and controlling a number of output states of the aircraft passenger suite, based on both the logic condition input and the at least one attribute.

According to a ninth aspect of the present invention, there is provided an aircraft passenger suite comprising an aircraft seat for use by a passenger, the aircraft passenger suite also comprising a controller for controlling a number of output states of the aircraft passenger suite, the controller comprising a first receiver operable to receive a logic condition input, wherein the logic condition input includes one or more preferences provided by a passenger of the aircraft passenger suite, and a second receiver operable to receive sensor data from sensor equipment, the sensor data providing an indication of one or more attributes of a passenger of the aircraft passenger suite. The controller is configured to control at least one of the output states of the aircraft passenger suite based on both the logic condition input and the sensor data.

It will of course be appreciated that features described in relation to one aspect of the present invention may be incorporated into other aspects of the present invention. For example, the method of the invention may incorporate any of the features described with reference to the apparatus of the invention and vice versa.

DESCRIPTION OF THE DRAWINGS

Embodiments of the present invention will now be described by way of example only with reference to the accompanying schematic drawings of which.

DETAILED DESCRIPTION

Figure 1:
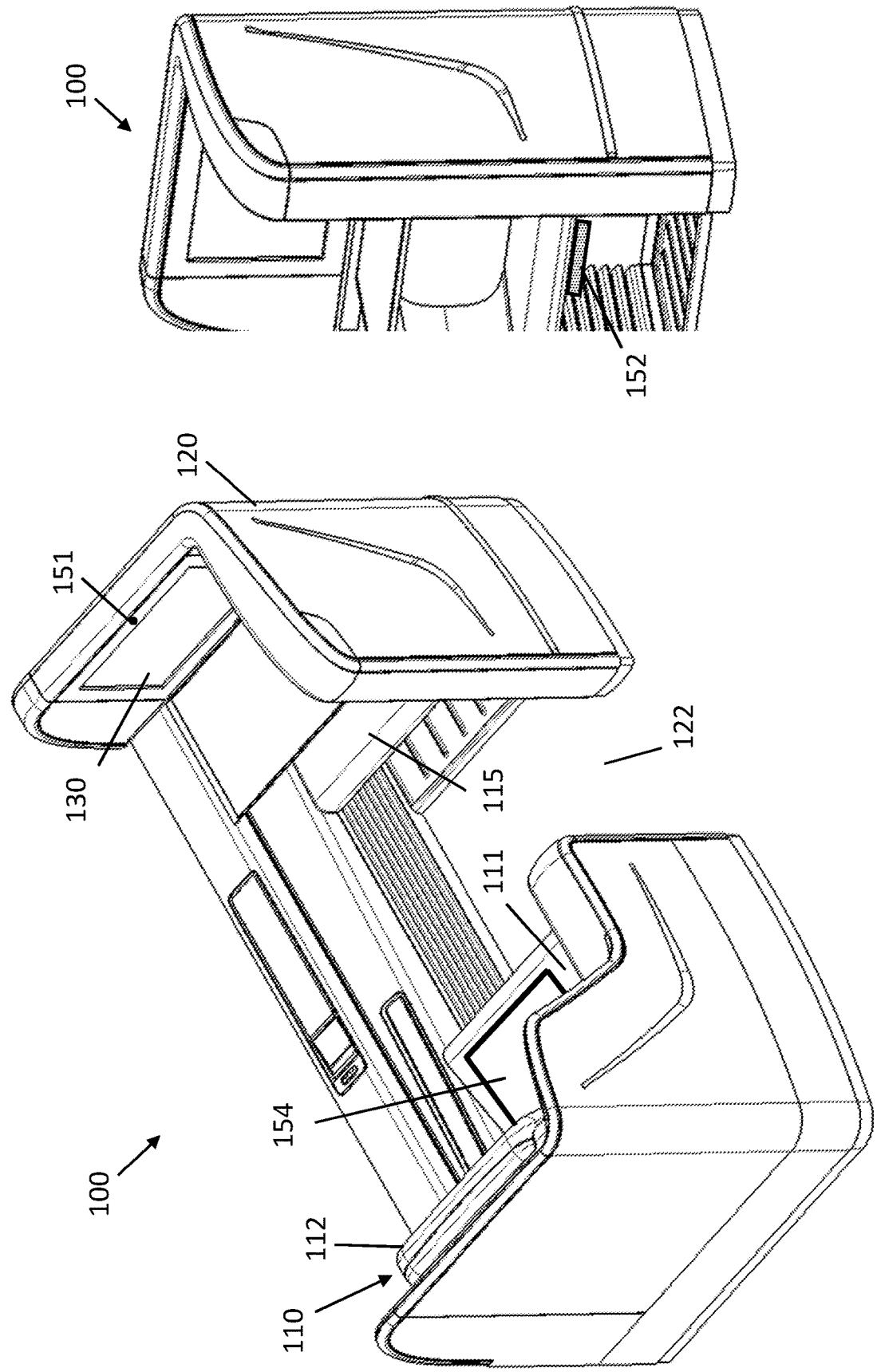
FIG. 1A shows a perspective view of an aircraft passenger suite, in accordance with a first embodiment of the invention.
FIG. 1B shows an alternative view of the aircraft passenger suite of FIG. 1A.

FIG. 1A shows a perspective view of an aircraft passenger suite 100 in accordance with a first embodiment of the present invention. FIG. 1B shows a portion of the suite 100 from an alternative perspective.

The suite 100 includes an aircraft seat 110. The seat 110 comprises a seat pan 111 and a back rest 112. The seat also comprises a leg rest (not shown). Also provided is an ottoman 115 located opposite the seat 110, which provides a footrest function for a passenger sat in the seat 110. The ottoman 115 may also make up part of a bed surface when the seat 110 is moved to a bed configuration. The suite 100 also includes a shell structure 120, or shroud, which defines the boundary of the suite 100. The shell structure 120 has a gap 122 to allow entrance/exit to the suite 100. The suite 100 also comprises a display device 130.

The suite 100 comprises a controller (not shown), which is configured to control output states of the suite 100 (e.g. to control the environment of the suite 100), as will be described in more detail below. The controller comprises a processing system. The processing system comprises one or more processors and/or memory. The controller also comprises one or more interfaces (which may be physical and/or logical interfaces) via which data can be received and/or outputted.

In this embodiment, the suite 100 comprises a video camera equipment 151 located above the display device 130, and facing the seat 110. The suite 100 also comprises a thermal imaging equipment 152 located beneath the ottoman 115. The suite 100 also comprises a pressure sensor 154 arranged within the seat pan 111. The video camera equipment 151, thermal imaging equipment 152 and pressure sensor 154 are each examples of sensor equipment. The sensor equipment provides a sensor input to the controller. That is, the video camera equipment 151 provides video data to the controller, the thermal imaging equipment 152 provides thermal image data to the controller and/or the pressure sensor 154 provides pressure sensor data to the controller. The sensor input provides an indication of at least one attribute of a passenger of the suite 100. The controller does the controlling of the output states based on a logic condition input received via a logic condition receiver of the controller, and the sensor input received from the sensor equipment.

The suite 100 may comprise more, fewer and/or different components in other examples. Similarly, the sensor equipment may comprise more, fewer and/or different components in other examples. The items shown in the suite 100 may be located in different positions within the suite 100 in other examples.

Figure 2:
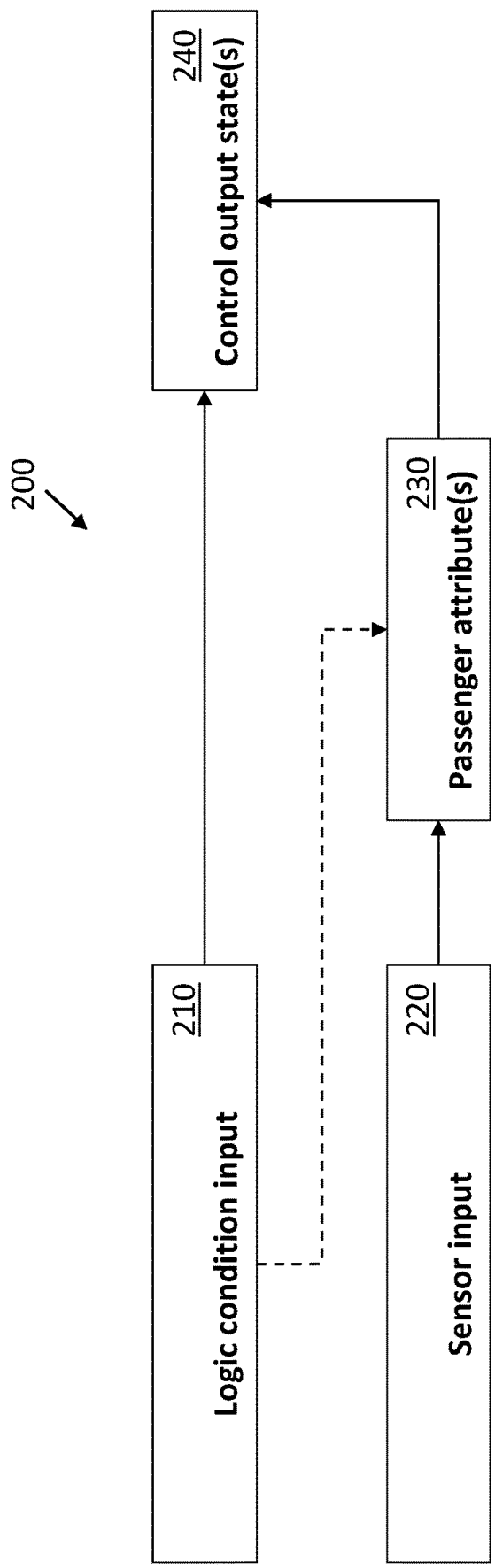
FIG. 2 shows schematically a control arrangement for use with any of the aircraft passenger suites described.

FIG. 2 shows schematically a control arrangement 200 for use in any of the aircraft passenger suites described herein, including the aircraft passenger suite 100 shown in FIG. 1.

The control arrangement 200 comprises multiple inputs and one or more controllable output states. The controller of the suite 100 is configured to receive the inputs and, based on those inputs, control the output states of the suite 100.

The inputs include a logic condition input 210 and a sensor input 220. Both the logic condition input 210 and the sensor input 220 are provided to the controller. The logic condition input 210 is received via a first receiver of the controller. The sensor input 220 is received via a second receiver of the controller. The controller determines one or more attributes 230 of a passenger of the suite 100, using the sensor input 220. In some cases, determining the passenger attribute(s) 230 is also based on the logic condition input 210. This is depicted using a dashed line in FIG. 2. In other cases, determining the passenger attribute(s) 230 is not based on the logic condition input 210. The controller then controls one or more output states 240 of the suite 100, based on the passenger attribute(s) 230 and the logic condition input 210. Hence, the output state(s) 240 is controlled based on both the logic condition input 210 and the sensor input 220.

In the following figures, specific examples of the control function of various aircraft passenger suites 100 will be given. Some of these examples are illustrated with aircraft passenger suites 100 that differ from the design of the suite 100 in FIG. 1. However, the features of the suites are similar, unless otherwise stated, and so will be described with reference to like reference numerals. Any of the control functions and/or arrangements described herein may be used with any of the suites described herein.

Figure 3:
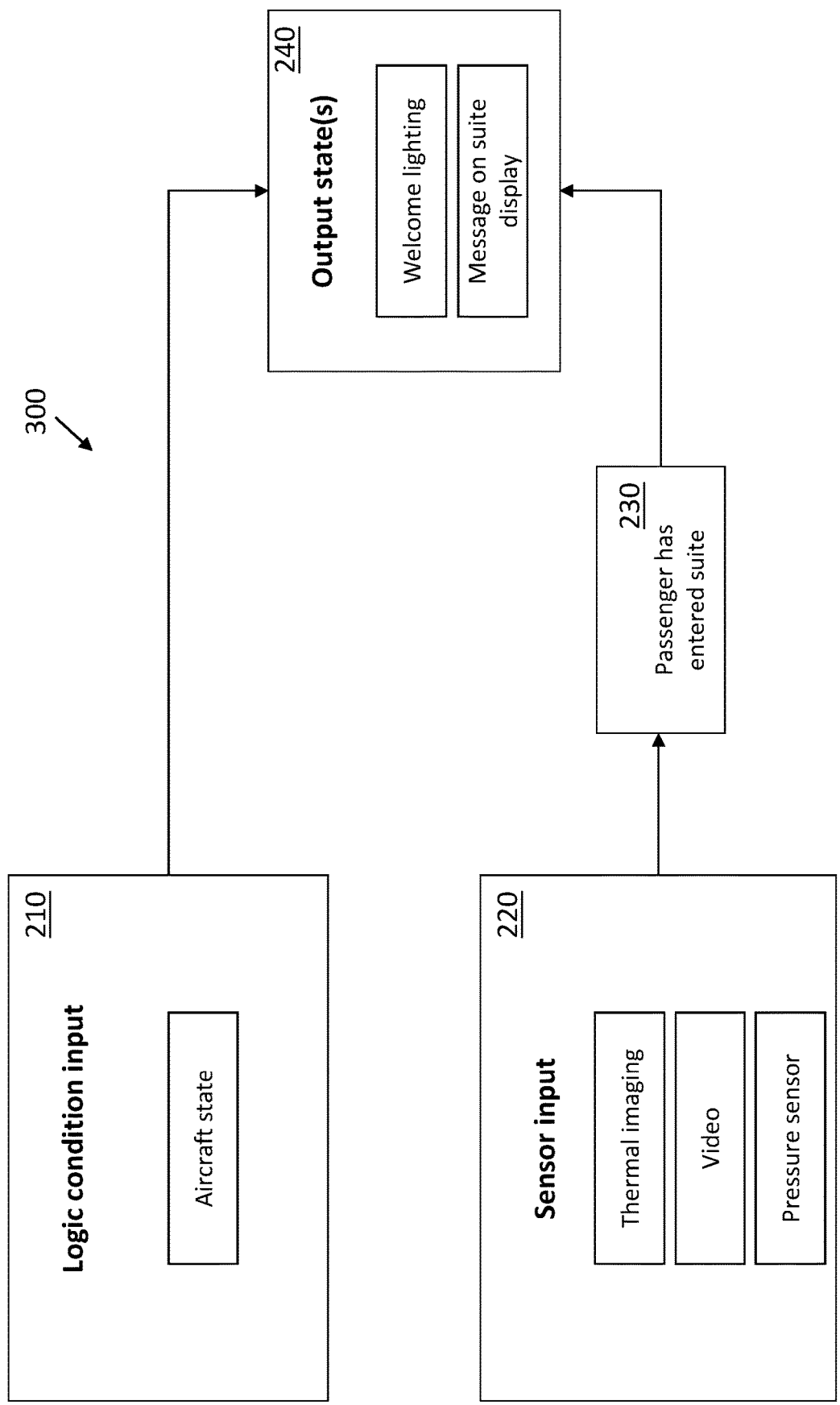
FIG. 3 shows schematically a control arrangement in accordance with the first embodiment.

FIG. 3 shows schematically a control arrangement 300 according to the first embodiment. In this embodiment, the logic condition input 210 includes an aircraft state. The sensor input 220 includes thermal imaging data obtained from a thermal imaging equipment, video data obtained from a video equipment, and/or pressure sensor data obtained from a pressure sensor. The sensor input 220 indicates that a passenger has entered the suite. The aircraft state is "boarding". Accordingly, the controller controls the output state such that a welcoming message is displayed and/or welcome lighting is turned on. As such, the controller changes the suite 100 by controlling the output state.

Figure 4:
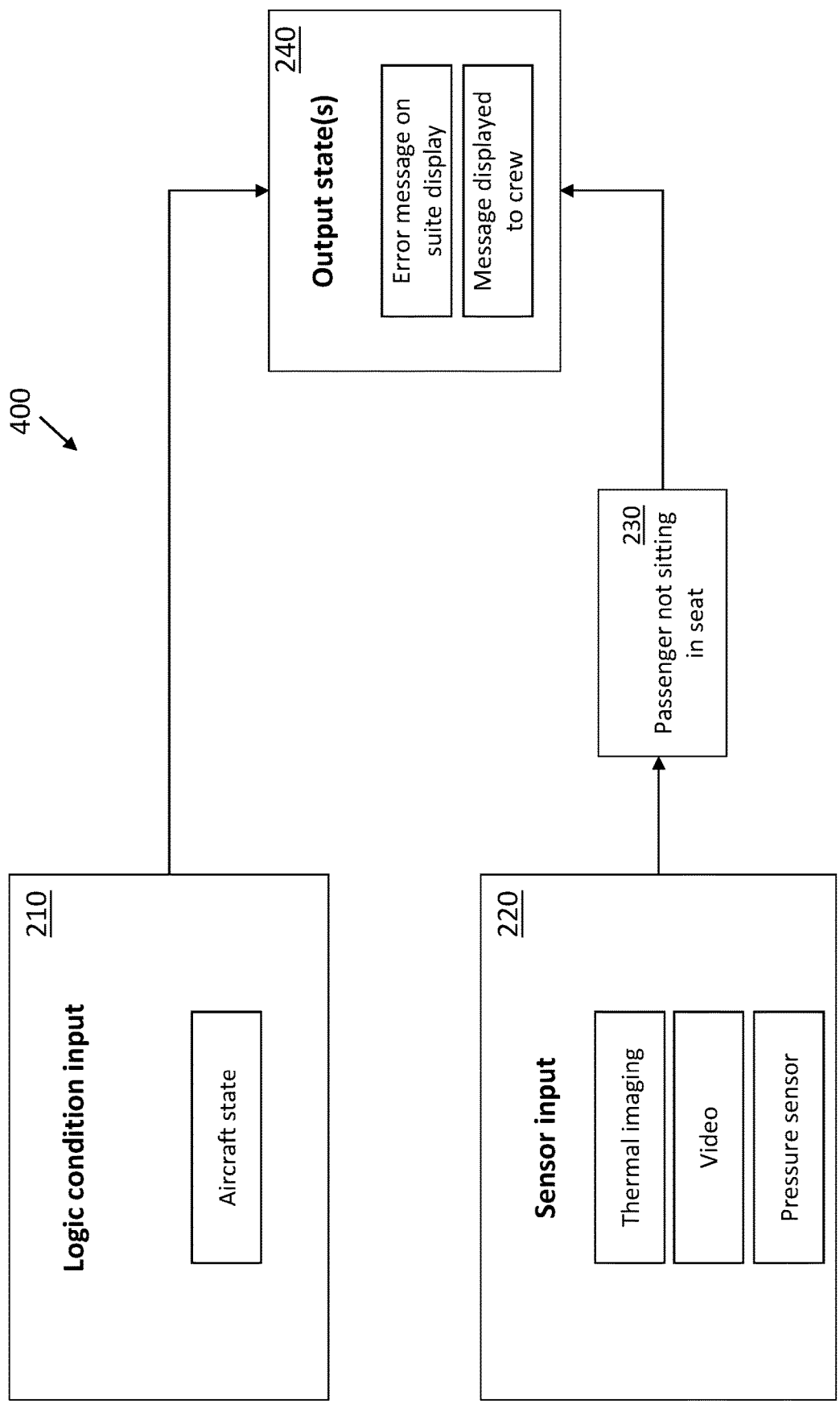
FIG. 4 shows schematically a control arrangement in accordance with a second embodiment.

FIG. 4 shows schematically a control arrangement 400 according to a second embodiment. In this embodiment, the logic condition input 210 includes an aircraft state. The sensor input 220 includes thermal imaging data obtained from a thermal imaging equipment, video data obtained from video equipment and/or pressure sensor data obtained from a pressure sensor. The sensor input 220 indicates that the passenger is not sitting in the seat 110. The aircraft state is "ready for TTL". Accordingly, the controller controls the output state such that a message/warning light within the suite 110 is turned on, and/or a message/warning is provided to the crew.

Figure 5:
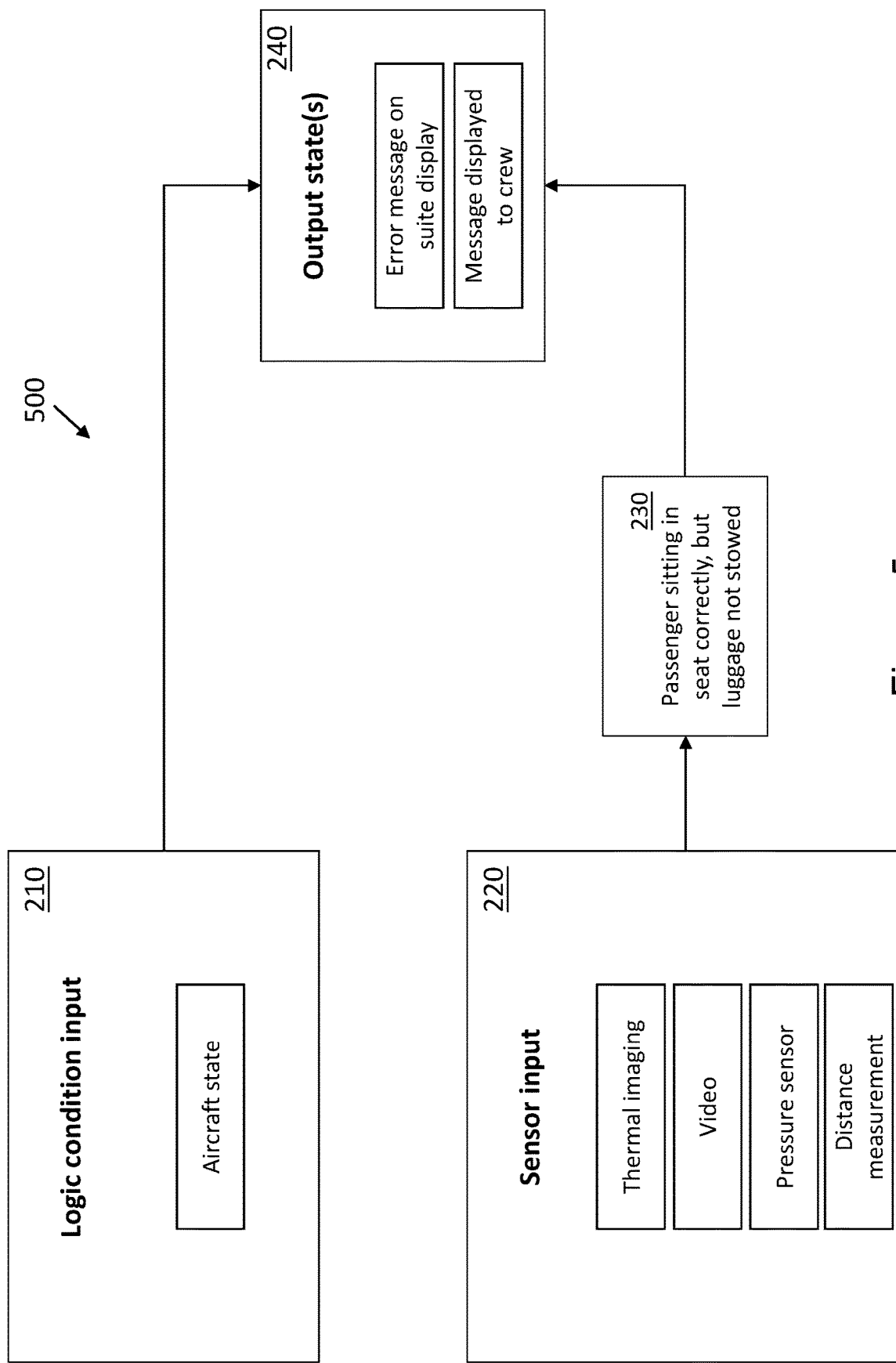
FIG. 5 shows schematically a control arrangement in accordance with a third embodiment.

FIG. 5 shows schematically a control arrangement 500 according to a third embodiment. In this embodiment, the logic condition input 210 includes an aircraft state. The sensor input 220 includes thermal imaging data obtained from a thermal imaging equipment, video data obtained from video equipment, pressure sensor data obtained from a pressure sensor and/or distance measurement data obtained from a distance sensor. The sensor input 220 indicates that the passenger is sitting in the seat 110 correctly, but that luggage is not stowed. The aircraft state is "ready for TTL". Accordingly, the controller controls the output state such that a message/warning light within the suite 110 is turned on, and/or a message/warning is provided to the crew.

Figure 6:
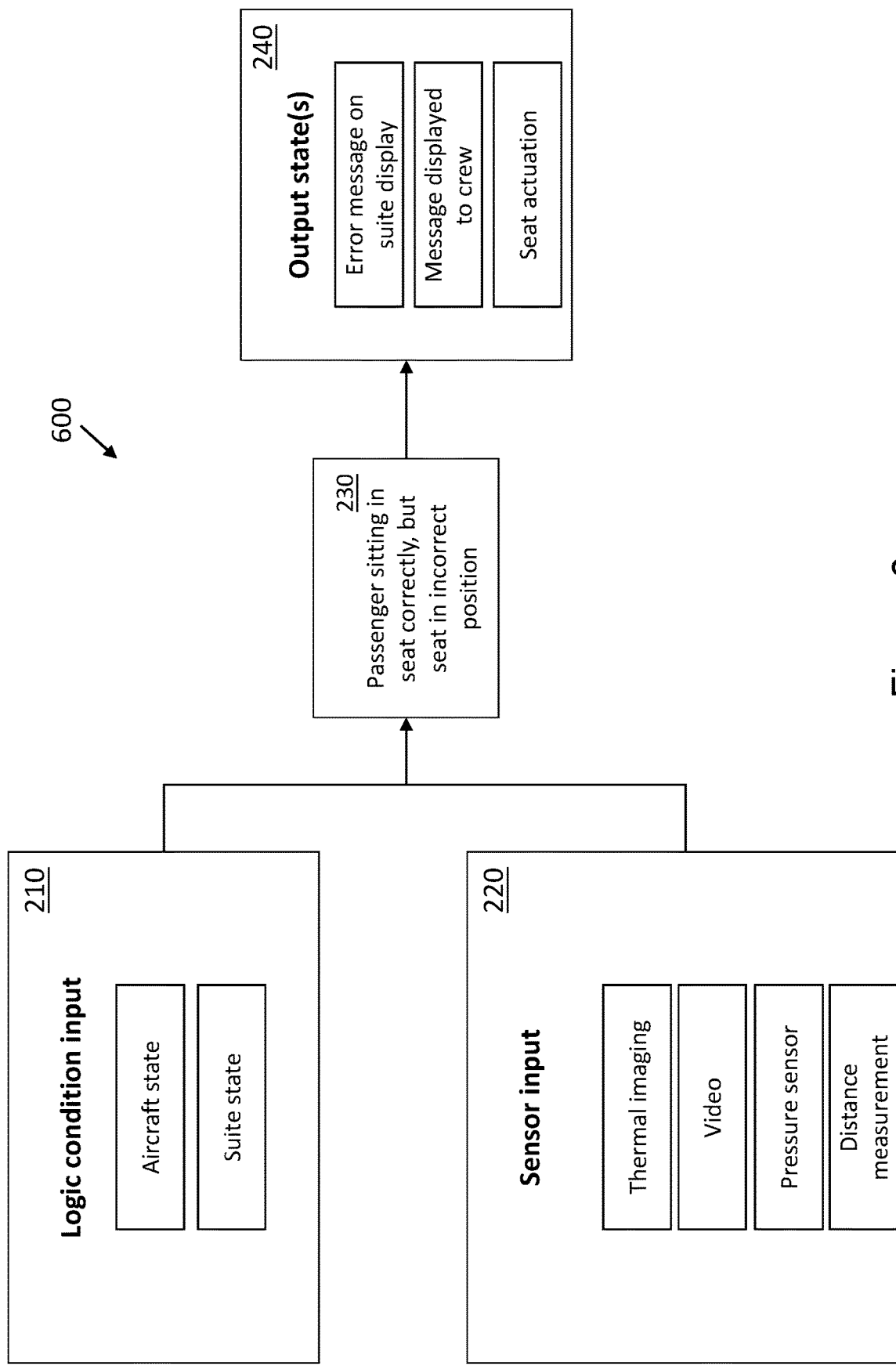
FIG. 6 shows schematically a control arrangement in accordance with a fourth embodiment.

FIG. 6 shows schematically a control arrangement 600 according to a fourth embodiment. In this embodiment, the logic condition input 210 includes an aircraft state and/or a suite state. The sensor input 220 includes thermal imaging data obtained from a thermal imaging equipment, video data obtained from video equipment, pressure sensor data obtained from a pressure sensor and/or distance measurement data obtained from a distance sensor. The sensor input 220 indicates that the passenger is sitting in the seat 110 correctly. The aircraft state is "ready for TTL". However, the suite state indicates that the seat is not positioned correctly for TTL. Accordingly, the controller controls the output state such that a message/warning light within the suite 110 is turned on, a message/warning is provided to the crew and/or automatic actuation of seat movement is performed.

Figure 7:
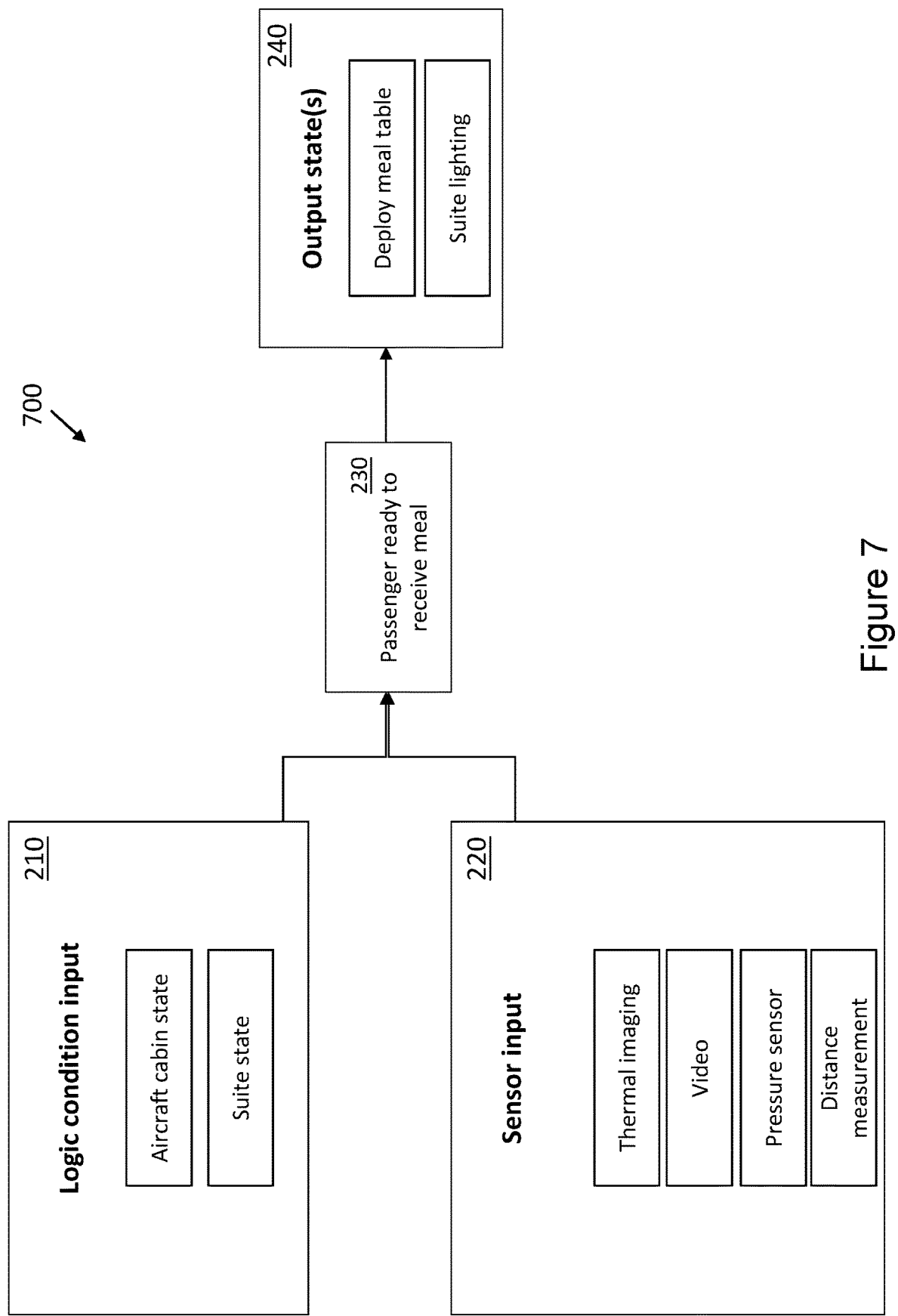
FIG. 7 shows schematically a control arrangement in accordance with a fifth embodiment.

FIG. 7 shows schematically a control arrangement 700 according to a fifth embodiment. In this embodiment, the logic condition input 210 includes an aircraft cabin state and/or a suite state. The sensor input 220 includes thermal imaging data obtained from a thermal imaging equipment, video data obtained from video equipment, pressure sensor data obtained from a pressure sensor and/or distance measurement data obtained from a distance sensor. The sensor input 220 indicates that the passenger is sitting in the seat 110 and ready to receive a meal. The cabin state is "meal time". The suite state is "meal table stowed". Accordingly, the controller controls the output state such that the meal table is deployed, and/or suite lighting is adjusted to focus light onto the meal table.

Figure 8:
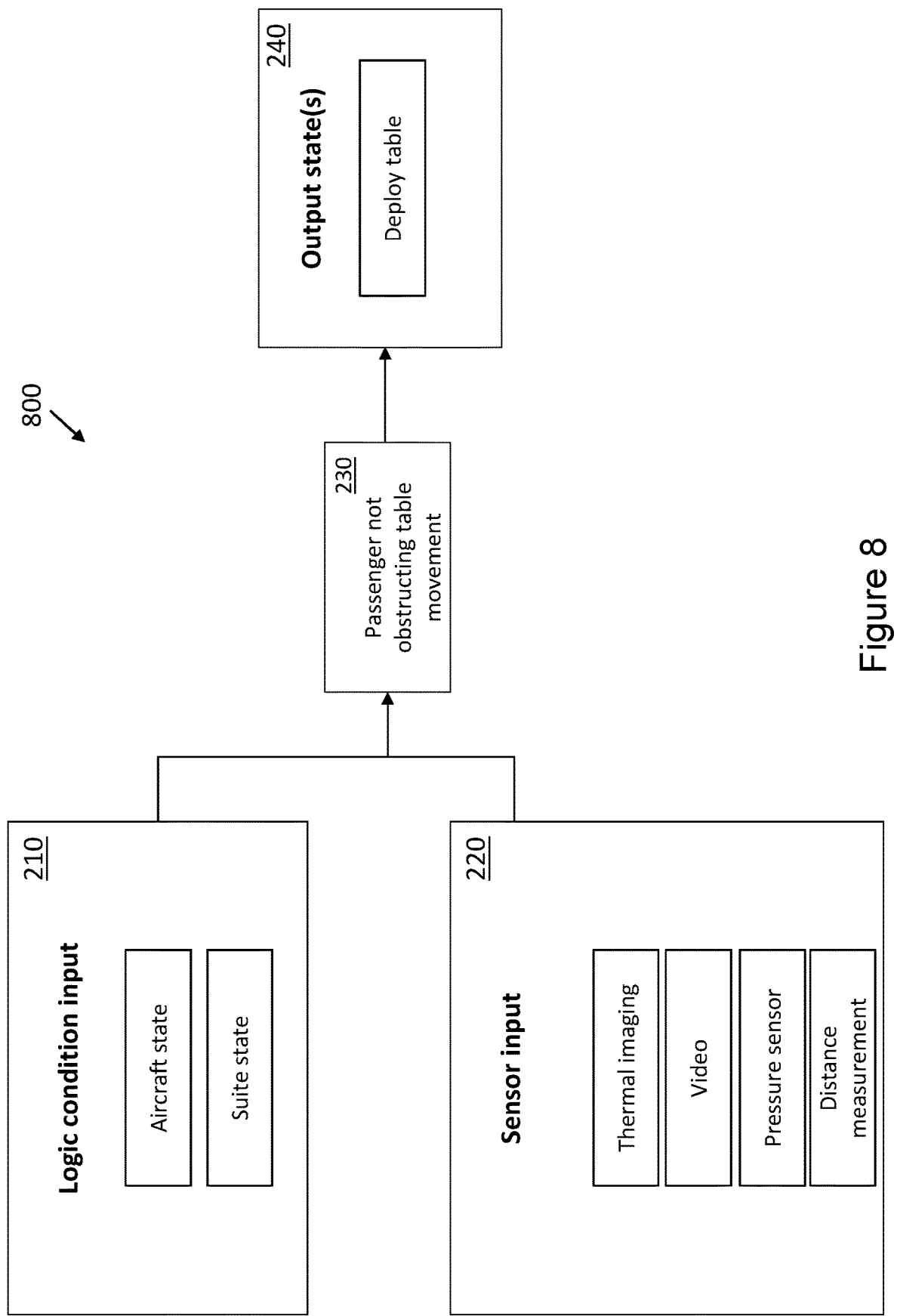
FIG. 8 shows schematically a control arrangement in accordance with a sixth embodiment.

FIG. 8 shows schematically a control arrangement 800 according to a sixth embodiment. In this embodiment, the logic condition input 210 includes an aircraft state and/or a suite state. The sensor input 220 includes thermal imaging data obtained from a thermal imaging equipment, video data obtained from video equipment, pressure sensor data obtained from a pressure sensor and/or distance measurement data obtained from a distance sensor. The sensor input 220 indicates that the passenger (or a part of the passenger) is not in a position which will obstruct movement of the meal table. The aircraft state is "in flight". The suite state is "meal table stowed". Accordingly, the controller controls the output state such that the meal table is deployed.

Figure 9:
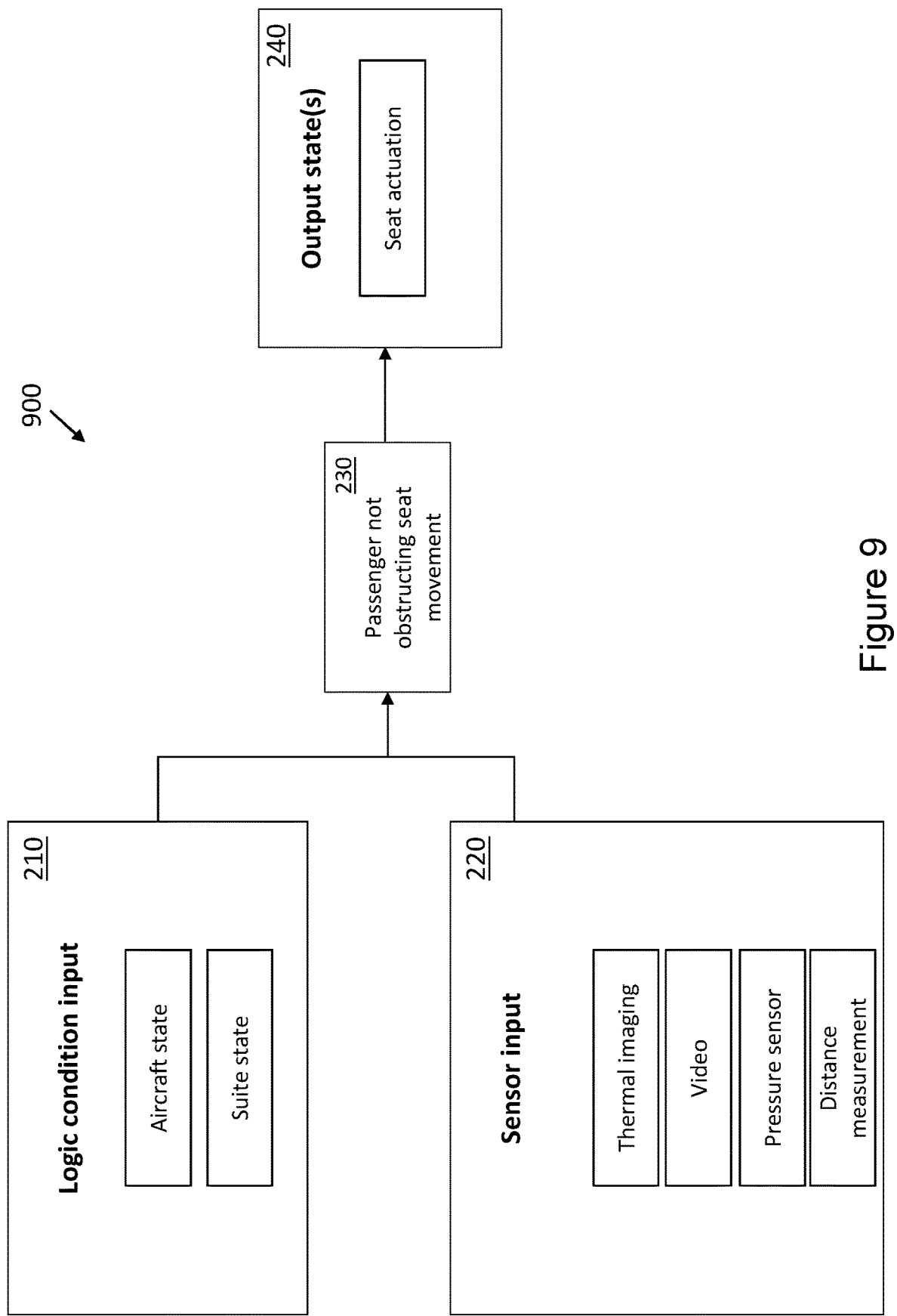
FIG. 9 shows schematically a control arrangement in accordance with a seventh embodiment.

FIG. 9 shows schematically a control arrangement 900 according to a seventh embodiment. In this embodiment, the logic condition input 210 includes an aircraft state and/or a suite state. The sensor input 220 includes thermal imaging data obtained from a thermal imaging equipment, video data obtained from video equipment, pressure sensor data obtained from a pressure sensor and/or distance measurement data obtained from a distance sensor. The sensor input 220 indicates that the passenger (or a part of the passenger) is not in a position which will obstruct movement of the seat towards the bed position. The aircraft state is "in flight". The suite state is "seat not in bed position". Accordingly, the controller controls the output state such that the seat is moved to the bed position.

Figure 10A:
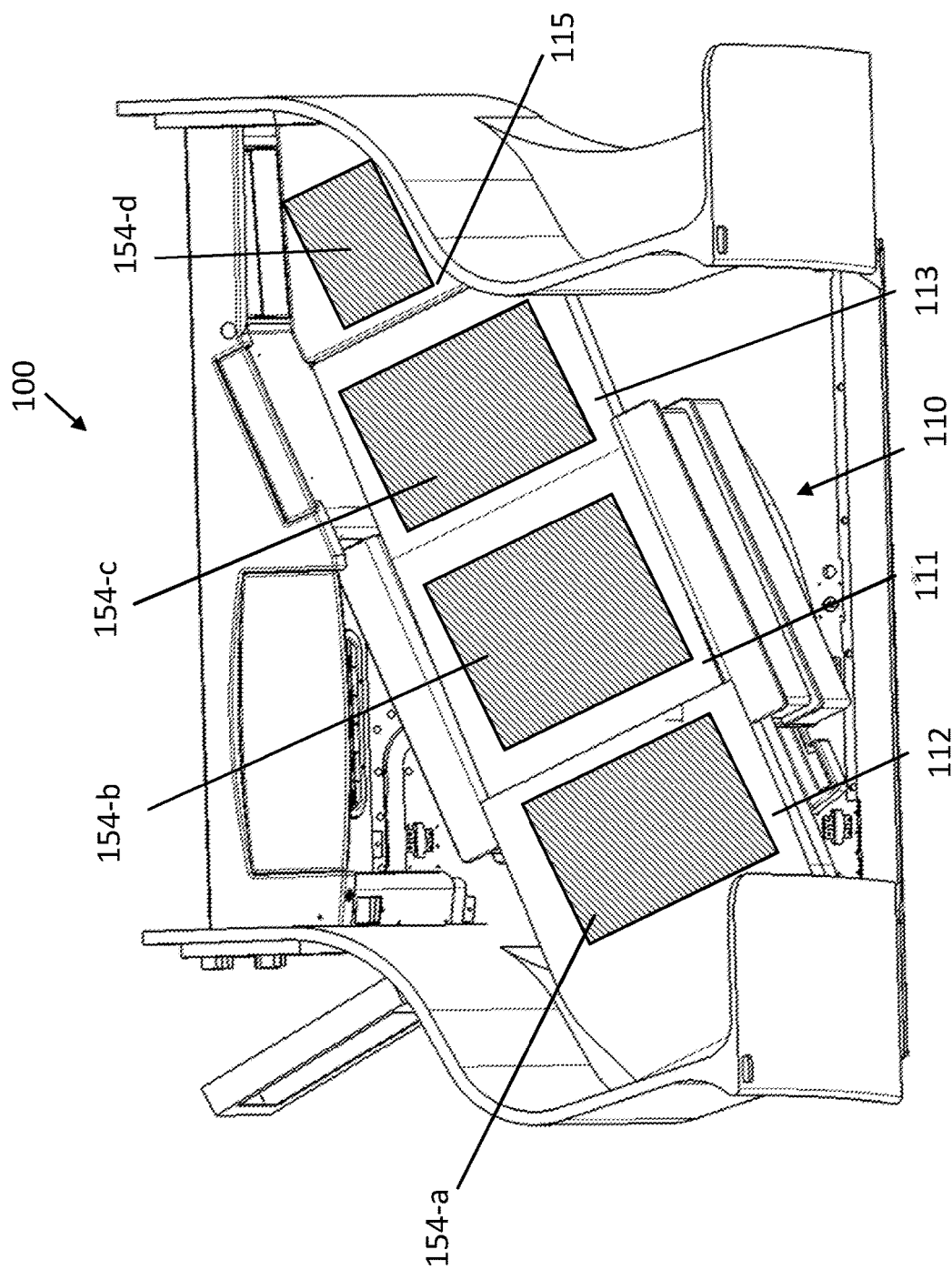
FIG. 10A shows a perspective view of an aircraft passenger suite in accordance with an eighth embodiment.

FIG. 10A shows a perspective view of aircraft suite 100 in accordance with a eighth embodiment of the invention. Here, the seat 110 is in a bed configuration. The seat 110 comprises a seat pan portion 111, a back rest portion 112, and a leg rest portion 113, which cooperatively form part of a bed. The ottoman 115 also forms part of the bed. Each of the portions of the seat 110 and/or the ottoman 115 include a support surface for supporting part of the passenger's body. In this embodiment, each of the portions of the seat 110 and the ottoman 115 comprise a respective pressure pad 154 (i.e. including pressure sensors). The pressure pads 154-a, 154-b, 154-c, 154-d are arranged under the support surfaces of the respective seat portions and ottoman.

Figure 10B:
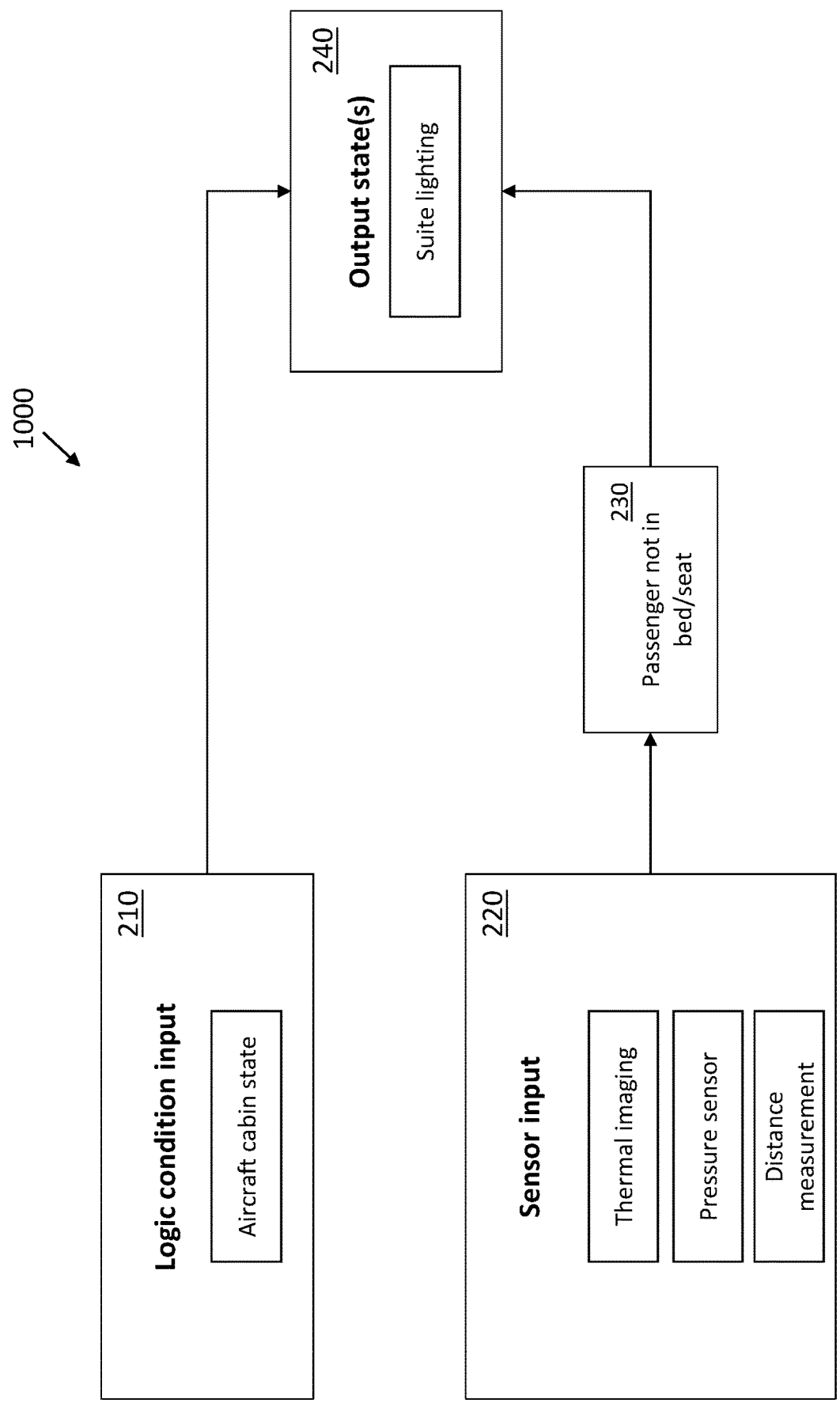
FIG. 10B shows schematically a control arrangement in accordance with the eighth embodiment.

FIG. 10B shows schematically a control arrangement 1000 according to the eighth embodiment. In this embodiment, the logic condition input 210 includes an aircraft cabin state. The sensor input 220 includes thermal imaging data obtained from a thermal imaging equipment, pressure sensor data obtained from a pressure sensor and/or distance measurement data obtained from a distance sensor. The cabin state is "lights dimmed for night-time". The sensor input 220 indicates that the passenger has got out of bed. Accordingly, the controller controls the output state such that a light is turned on within the suite 100.

Figure 11A:
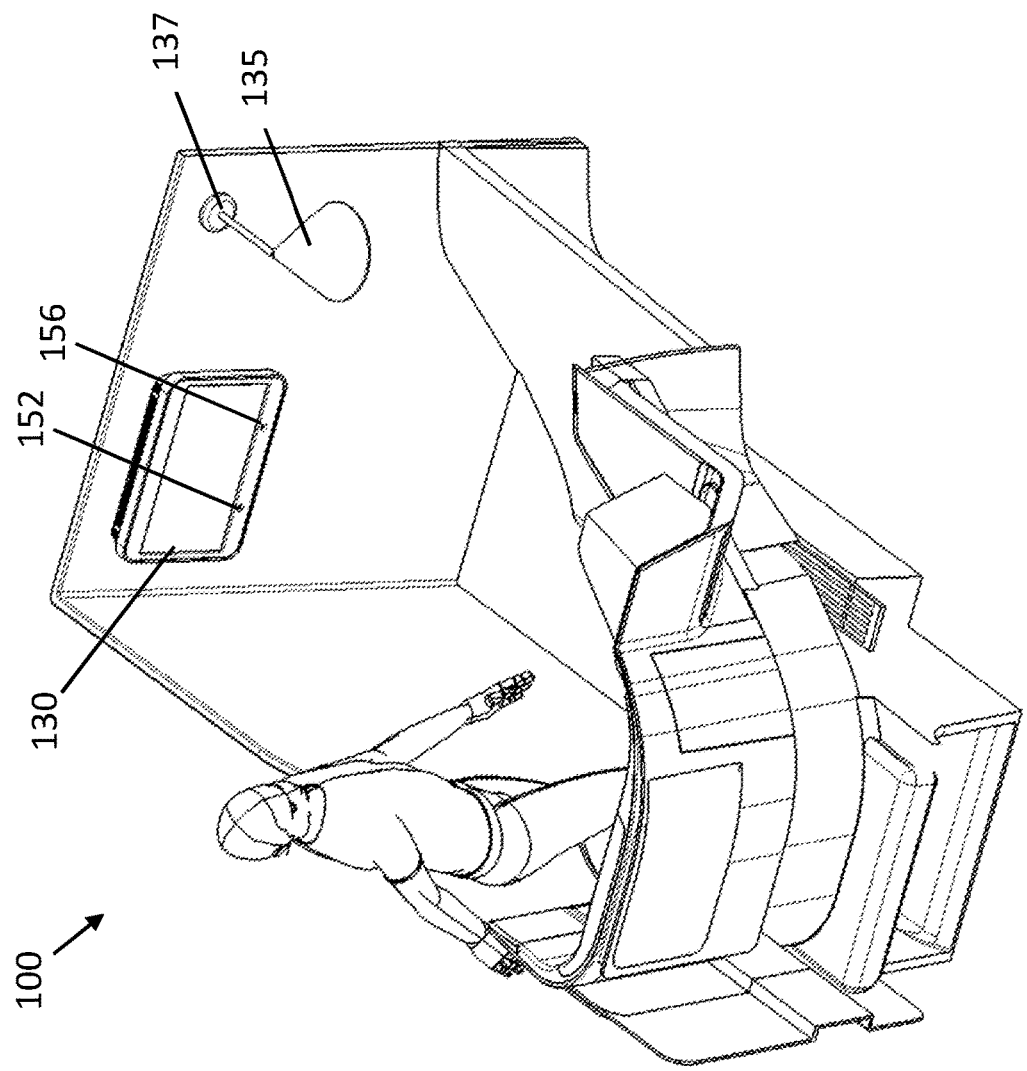
FIG. 11A shows a perspective view of an aircraft passenger suite in accordance with a ninth embodiment.
Figure 11B:
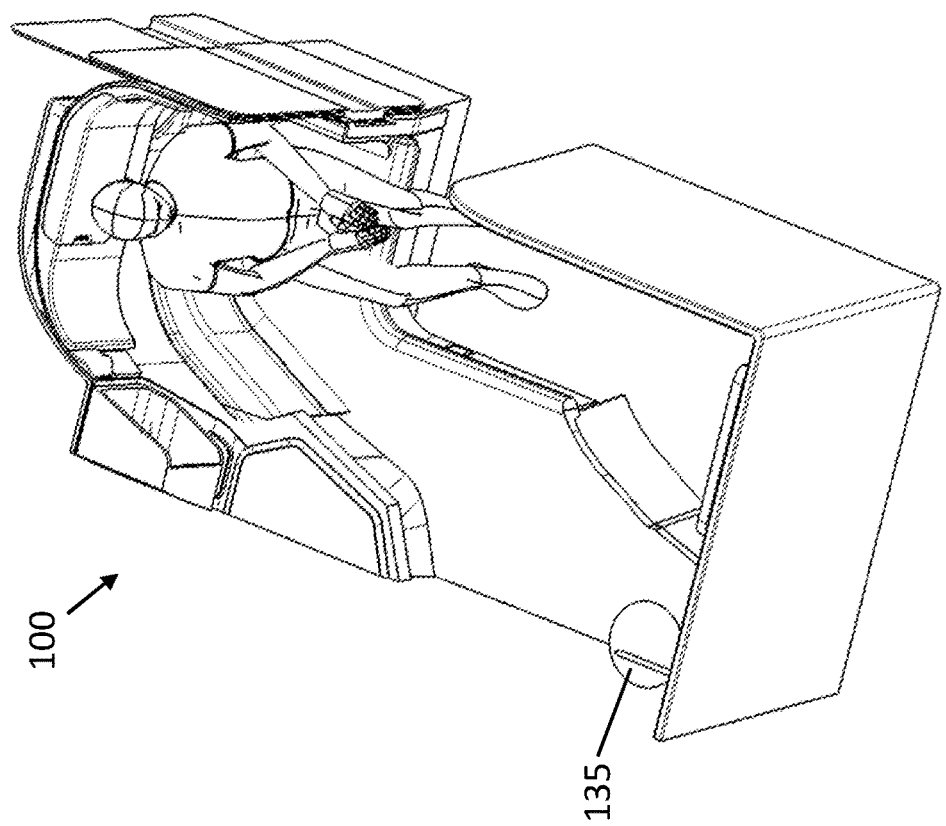
FIG. 11B shows an alternative view of the aircraft passenger suite of FIG. 11A.

FIG. 11A shows a perspective view of an aircraft suite 100 in accordance with a ninth embodiment of the invention. FIG. 11B shows an alternative view of the suite 100 shown in FIG. 11A. In this embodiment, the suite 100 comprises a feature light 135. The feature light 135 may be used to aid passenger comfort. For example, blue or green light may be emitted from the feature light 135, which may reduce passenger anxiety. The suite 100 also comprises a pulsating light 137. The pulsating light 137 may be used to aid passenger comfort, e.g. by causing emitted light to pulsate at a particular rate or rhythm.

In this embodiment, a thermal image sensor 152 is installed in a pre-existing screw hole underneath the display device 130. A breathing rate sensor 156 is installed in a second pre-existing screw hole underneath the display device 130. The pre-existing screw holes are comprised in the housing of the display device 130. Using pre-existing screw holes to mount sensors facilitates retrofitting of existing suites with sensor equipment. Further, such an arrangement is relatively unobtrusive and/or spatially efficient.

Figure 11C:
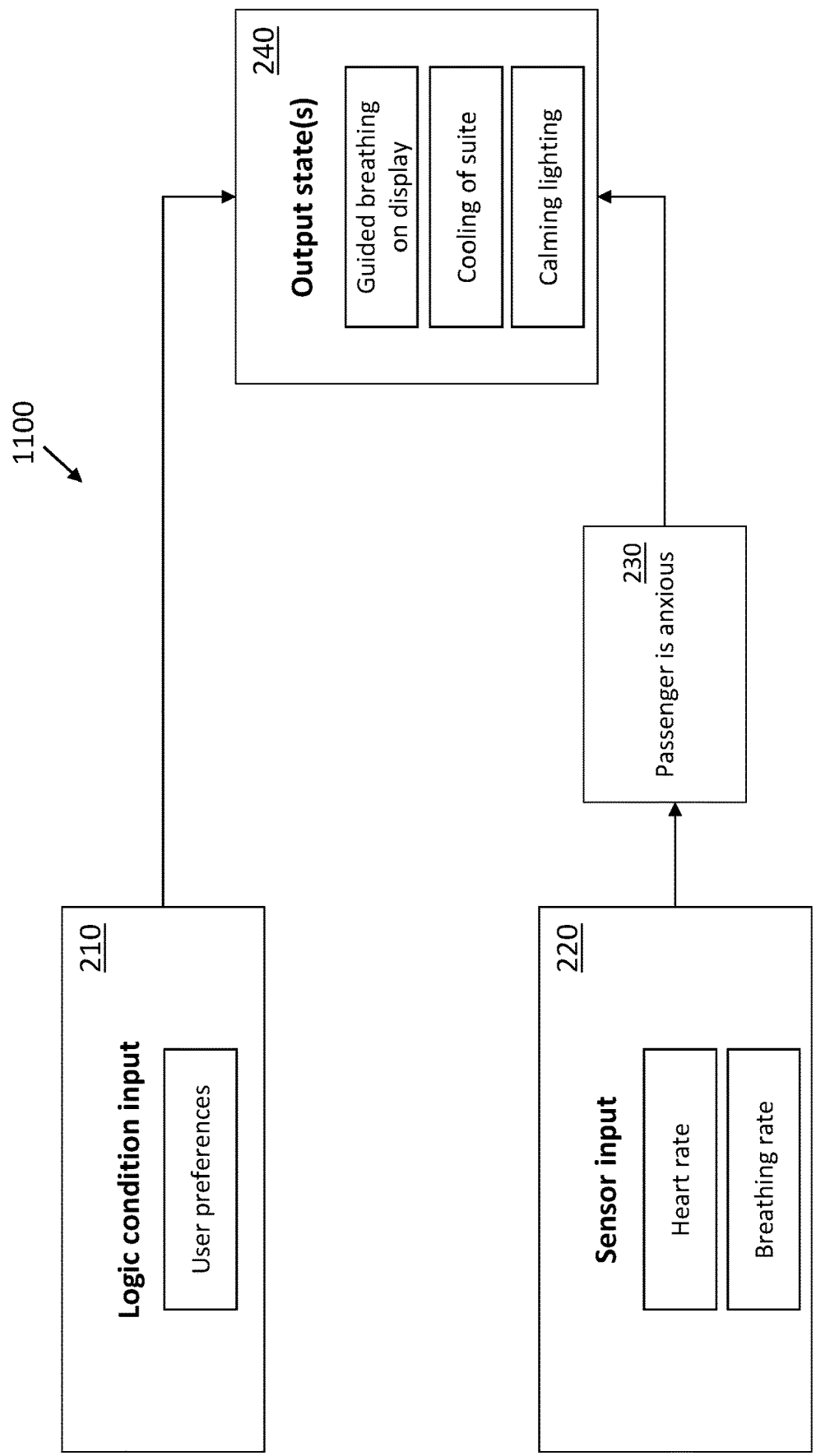
FIG. 11C shows schematically a control arrangement in accordance with the ninth embodiment.

FIG. 11C shows schematically a control arrangement 1100 according to the ninth embodiment. In this embodiment, the logic condition input 210 includes one or more user preferences. The sensor input 220 includes heart rate data obtained from a heart rate sensor, and/or breathing rate data obtained from a breathing rate sensor. The sensor input 220 indicates that the passenger is anxious. The logic condition input 210 indicates that the passenger has provided consent. Accordingly, the controller controls the output state such that the suite 100 is cooled, suite lighting is adjusted and/or a guided breathing pattern is shown to the passenger. Controlling the output state may involve controlling (e.g. turning on and/or adjusting) the feature light 135 and/or the pulsating light 137.

Figure 12A:
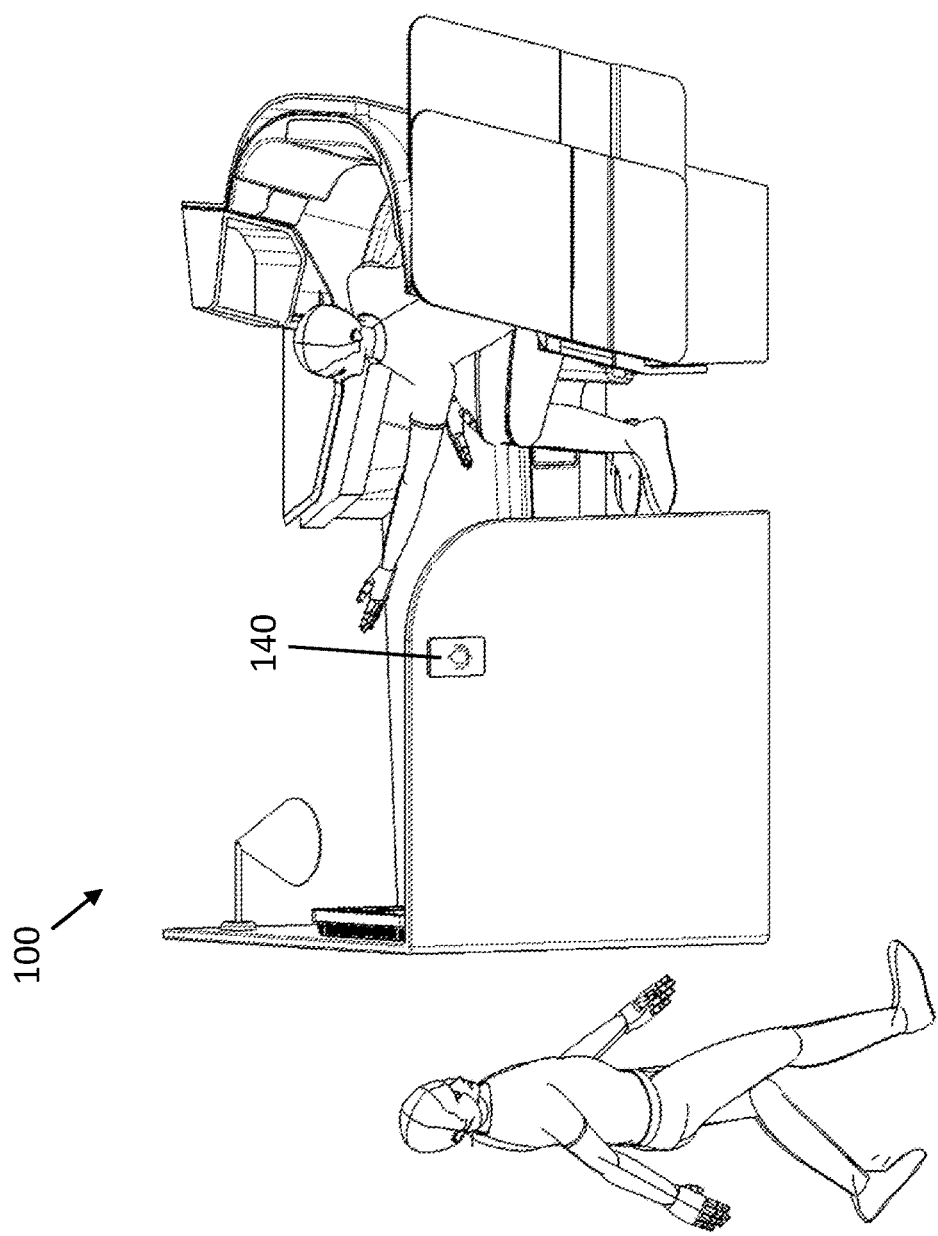
FIG. 12A shows a side view of an aircraft passenger suite in accordance with a tenth embodiment.

FIG. 12A shows a side view of an aircraft suite 100 in accordance with a tenth embodiment of the invention. Here, a display 140 is provided on an exterior surface of the shell structure 120. The display 140 is configured to display an indication of whether or not the passenger of the suite 100 requires medical assistance.

Figure 12B:
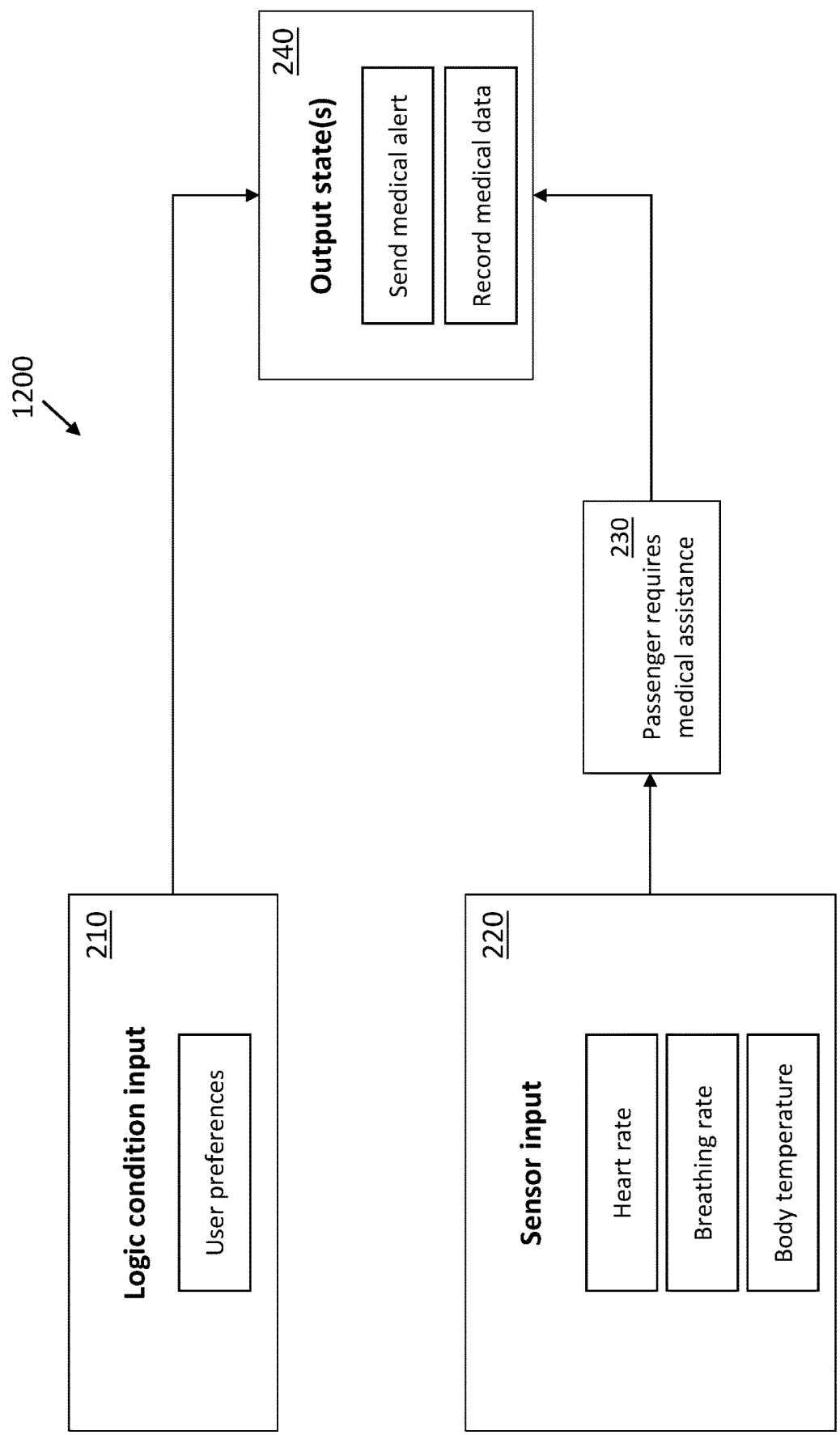
FIG. 12B shows schematically a control arrangement in accordance with the tenth embodiment.

FIG. 12B shows schematically a control arrangement 1200 according to the tenth embodiment. In this embodiment, the logic condition input 210 includes one or more user preferences. The sensor input 220 includes heart rate data obtained from a heart rate sensor, breathing rate data obtained from a breathing rate sensor and/or body temperature data obtained from a body temperature sensor. The sensor input 220 indicates that the passenger requires medical attention. The logic condition input 210 indicates that the passenger has provided consent. Accordingly, the controller controls the output state such that an indication that the passenger requires medical assistance is provided, and/or the medical data of the passenger is recorded for use by the crew and/or medical support on the ground. The indication may be displayed, e.g. via the display 140 outside the suite 100.

Figure 13:
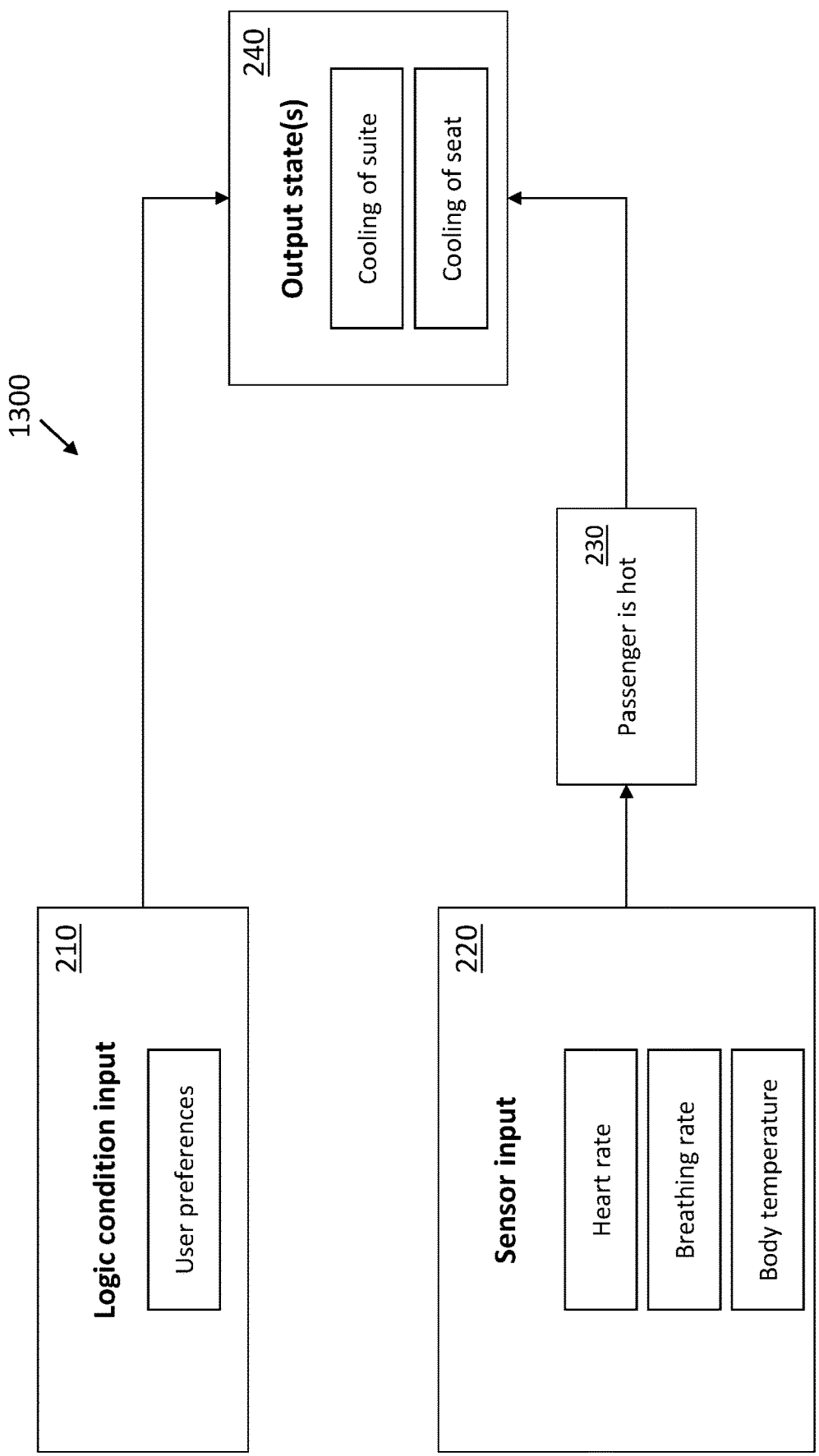
FIG. 13 shows schematically a control arrangement in accordance with an eleventh embodiment.

FIG. 13 shows schematically a control arrangement 1300 according to an eleventh embodiment. In this embodiment, the logic condition input 210 includes one or more user preferences. The sensor input 220 includes heart rate data obtained from a heart rate sensor, breathing rate data obtained from a breathing rate sensor and/or body temperature data obtained from a body temperature sensor. The sensor input 220 indicates that the passenger is hotter than expected. The logic condition input 210 indicates that the passenger has provided consent. Accordingly, the controller controls the output state such that the suite 100 is cooled and/or the seat 110 is cooled.

Figure 14:
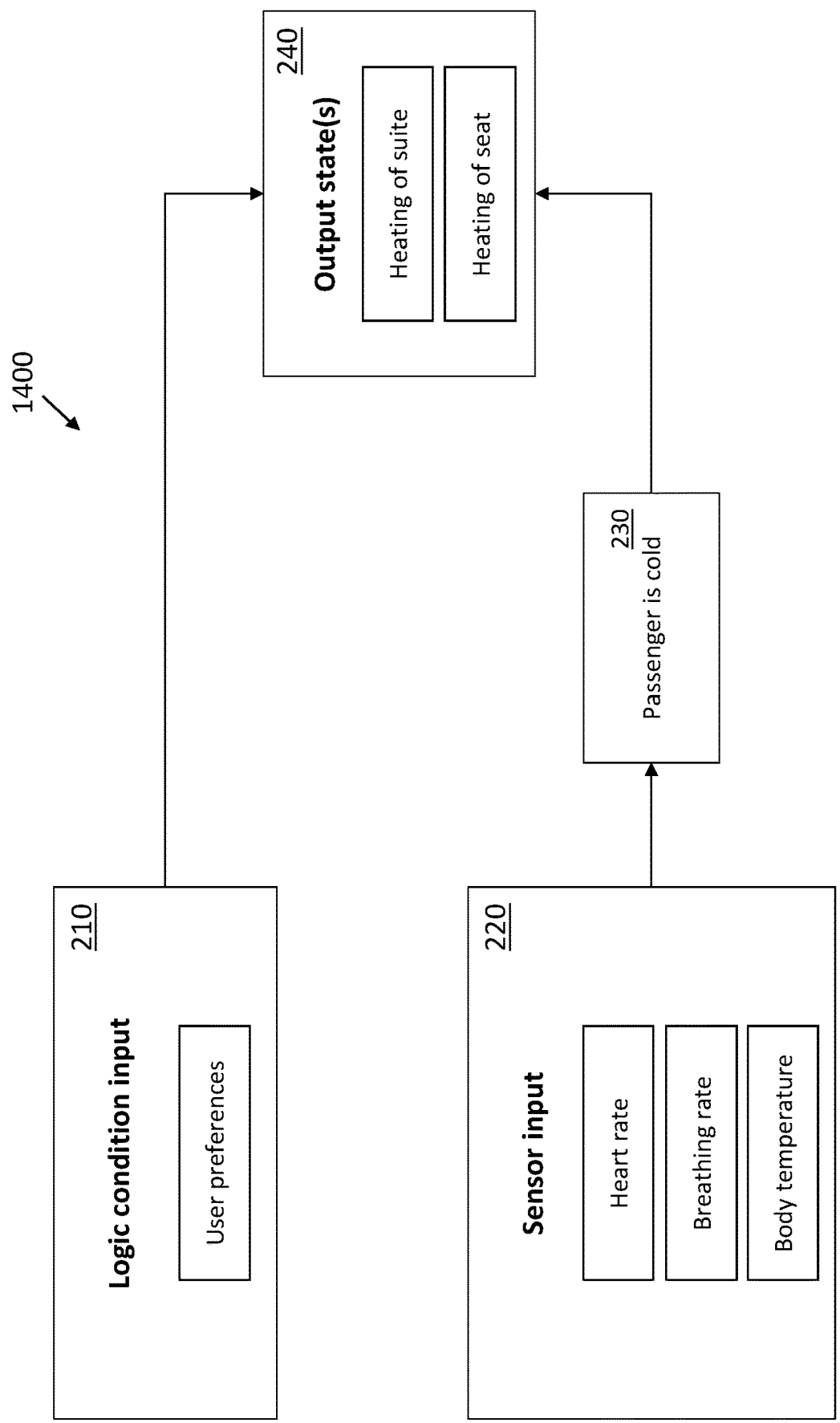
FIG. 14 shows schematically a control arrangement in accordance with a twelfth embodiment.

FIG. 14 shows schematically a control arrangement 1400 according to a twelfth embodiment. In this embodiment, the logic condition input 210 includes one or more user preferences. The sensor input 220 includes heart rate data obtained from a heart rate sensor, breathing rate data obtained from a breathing rate sensor and/or body temperature data obtained from a body temperature sensor. The sensor input 220 indicates that the passenger is colder than expected. The logic condition input 210 indicates that the passenger has provided consent. Accordingly, the controller controls the output state such that the suite 100 is heated and/or the seat 110 is heated.

Figure 15:
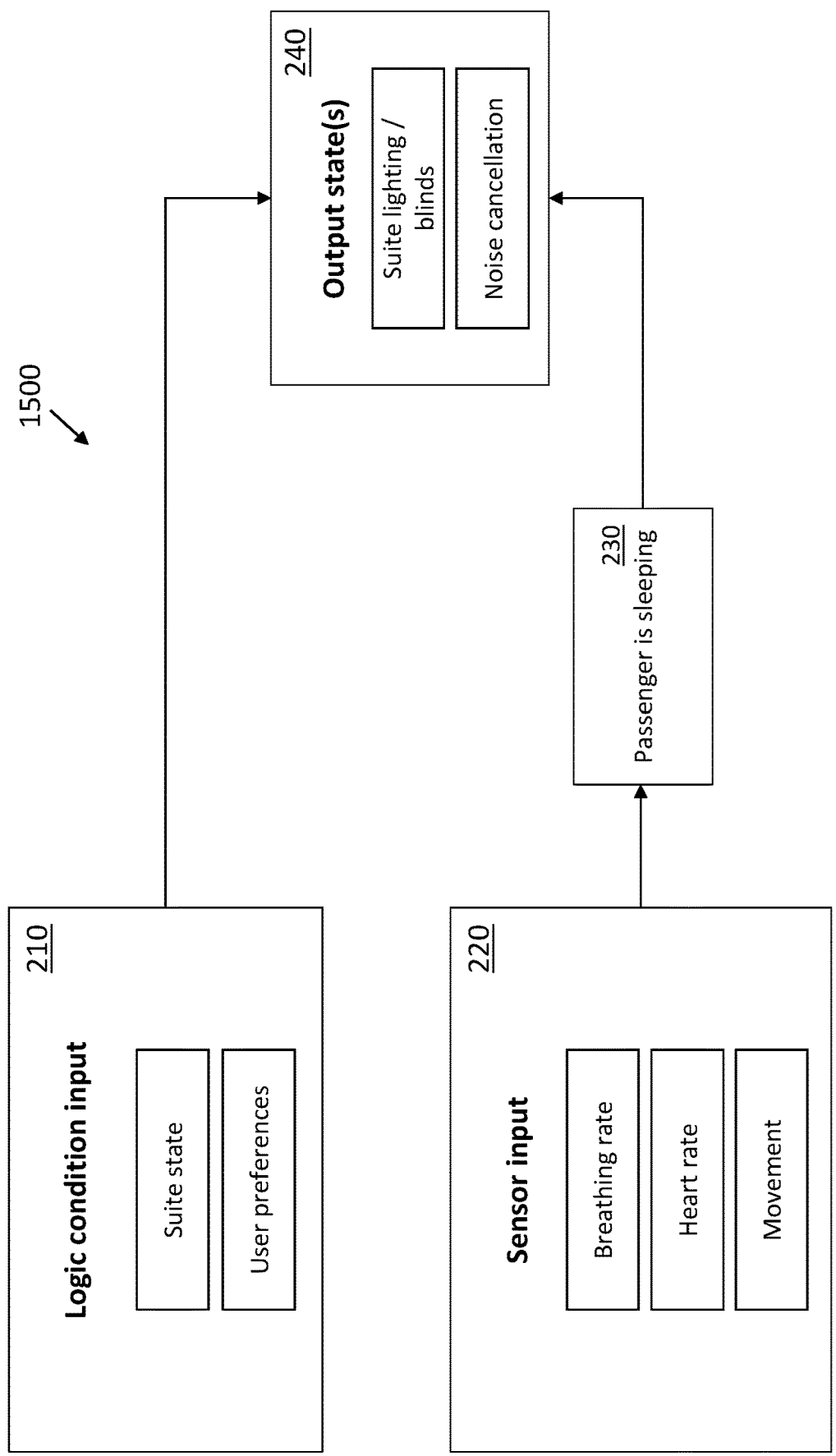
FIG. 15 shows schematically a control arrangement in accordance with a thirteenth embodiment.

FIG. 15 shows schematically a control arrangement 1500 according to a thirteenth embodiment. In this embodiment, the logic condition input 210 includes an aircraft suite state and/or one or more user preferences. The sensor input 220 includes heart rate data obtained from a heart rate sensor, breathing rate data obtained from a breathing rate sensor and/or movement data (e.g. obtained from one or more pressure sensors or image sensors). The sensor input 220 indicates that the passenger is sleeping. The logic condition input 210 indicates that the passenger has provided consent. The aircraft suite state is "seat in bed configuration". Accordingly, the controller controls the output state such that a lighting level within the suite 100 is adjusted, blinds are adjusted and/or noise cancellation is turned on.

Figure 16:
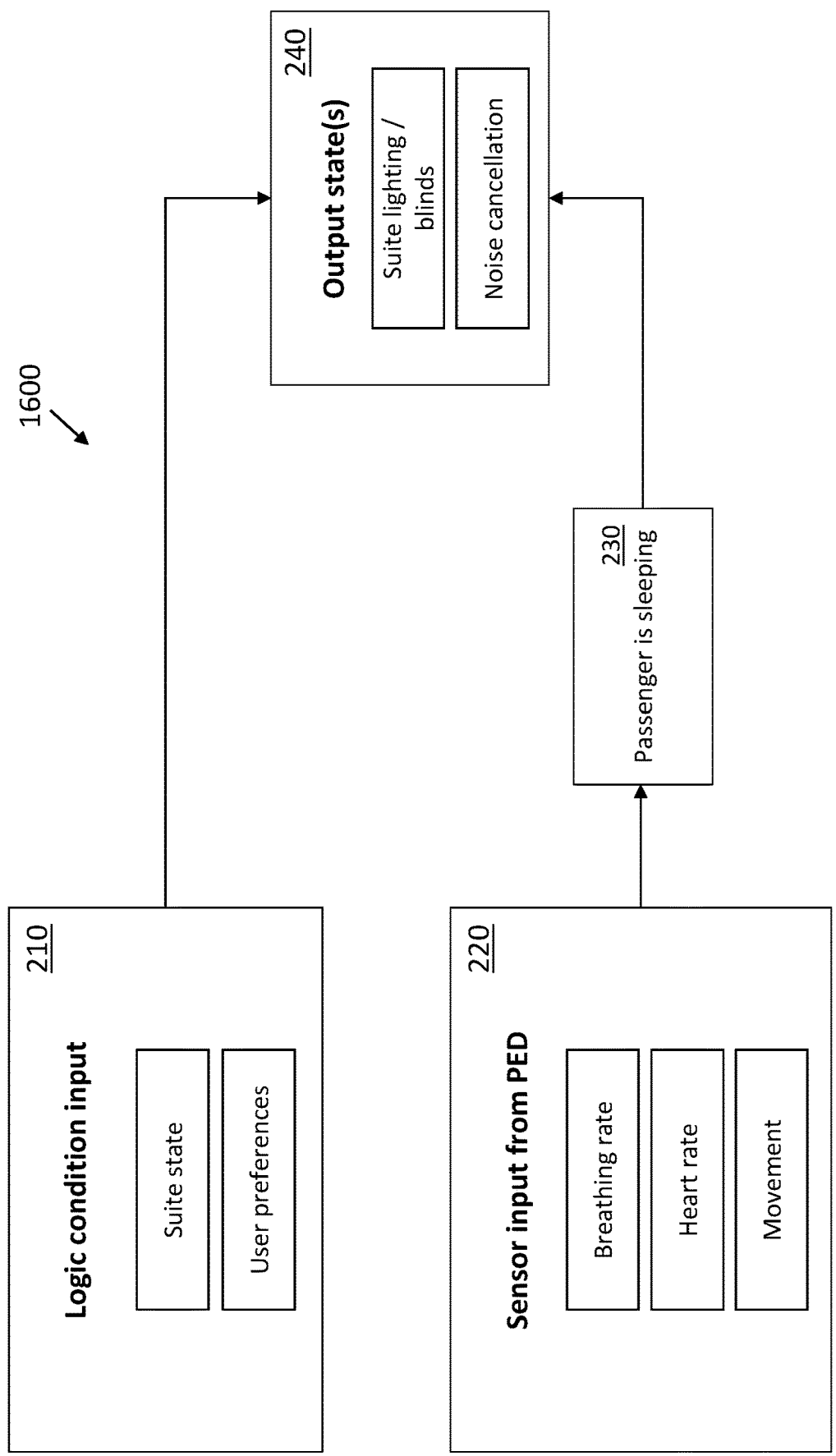
FIG. 16 shows schematically a control arrangement in accordance with a fourteenth embodiment.

FIG. 16 shows schematically a control arrangement 1600 according to a fourteenth embodiment. The control arrangement 1600 is similar to that shown in FIG. 15. In this case, however, the sensor input 220 is received from a personal electronic device of the passenger. Therefore, in this example, the sensor equipment does not form part of the suite 100. A breathing rate sensor, heart rate sensor and/or movement sensor provided in a personal electronic device of the passenger are used to obtain sensor data, which is then sent to the controller of the suite 100. The controller receives sensor input from such sensors, and uses the sensor input, along with the logic condition input, to control the output states of the suite 100. The sensor input 220 indicates that the passenger is sleeping. The logic condition input 210 indicates that the passenger has provided consent. The aircraft suite state is "seat in bed configuration". Accordingly, the controller controls the output state such that a lighting level within the suite 100 is adjusted, blinds are adjusted and/or noise cancellation is turned on. It should be noted that sensor data generated by other types of sensor may be received from a personal electronic device, may be combined with other logic condition inputs, and/or may be used to control other output states of the suite 100, in other examples.

Figure 17:
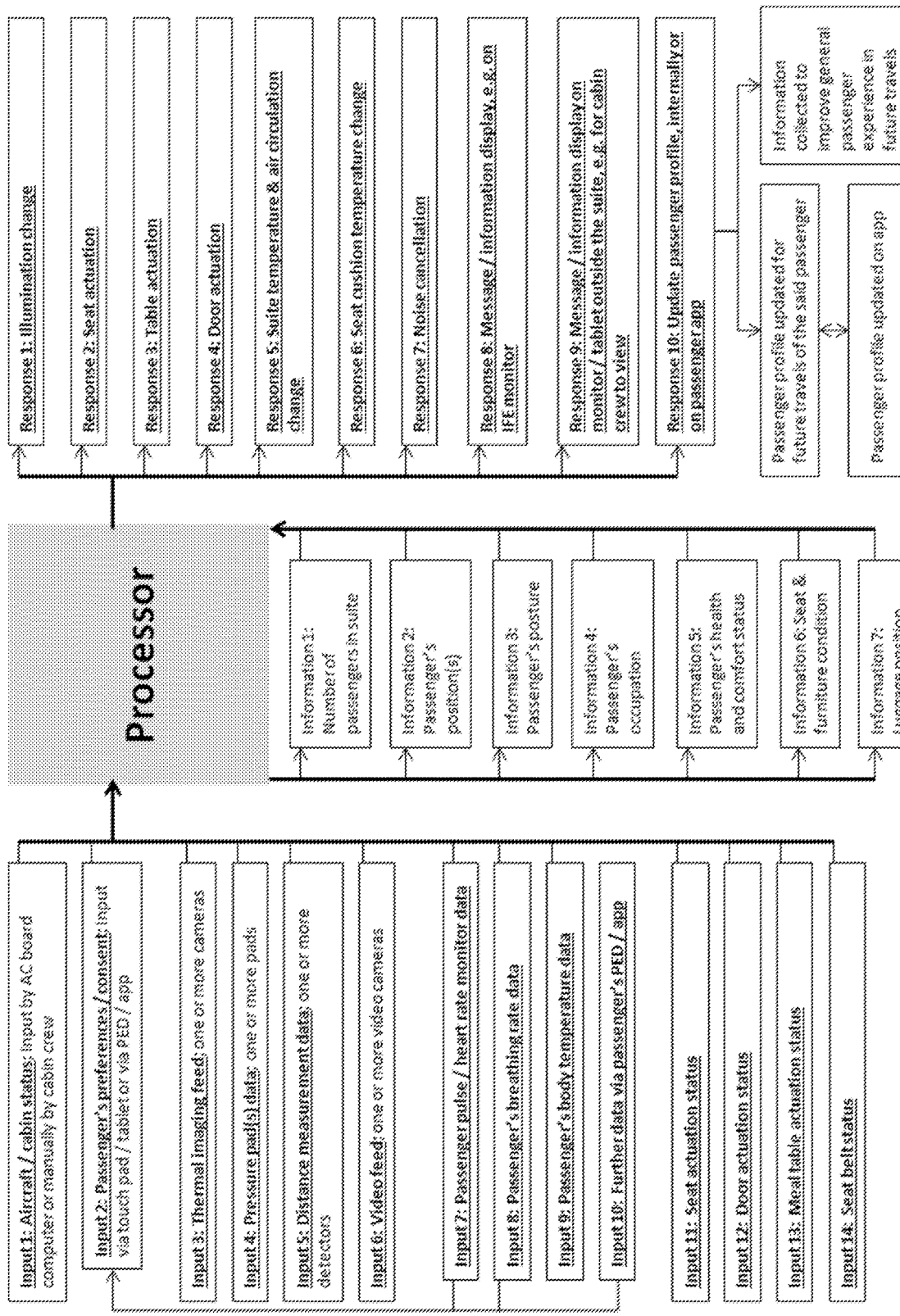
FIG. 17 shows schematically a control arrangement for use with any of the aircraft passenger suites described.

FIG. 17 shows schematically a control arrangement for use within any of the aircraft suites described. The control arrangement comprises multiple inputs (on the left hand side of the figure), a processor (in the middle) and a number of outputs or responses (on the right hand side).

The inputs can include one or more of: an aircraft/cabin status, which may be input via an on-board computer or by cabin crew; passenger preferences and/or consent, which may be input via a touch pad, tablet or personal electronic device; a thermal imaging feed, received from one or more cameras; pressure pad data, received from one or more pressure pads; distance measurement data, received from one or more distance sensors; a video feed, received from one or more video cameras; passenger pulse and/or heart rate monitor data; passenger breathing rate data; passenger body temperature data; further data received via a personal electronic device; a seat actuation status; a door actuation status; a meal table actuation status; and/or a seat belt status.

The processor is configured to receive one or more inputs from those described above, and determine information that is useable to generate a response. Such information can include one or more of: a number of passengers in the suite; the position of the passenger; the posture of the passenger; the occupation of the suite; a health and/or comfort status of the passenger; a furniture condition; and a luggage position.

The outputs controlled by the processor, based on the inputs and the information determined, can include one or more of: an illumination change; seat actuation; table actuation; door actuation; suite temperature and/or air circulation change; seat cushion temperature change; noise cancellation; a message displayed within the suite; a message displayed outside the suite; and/or updating a passenger profile.

Whilst the present invention has been described and illustrated with reference to particular embodiments, it will be appreciated by those of ordinary skill in the art that the invention lends itself to many different variations not specifically illustrated herein. By way of example only, certain possible variations will now be described.

In examples described above, the sensor input provides an indication of one or attributes of a passenger. In other examples, the sensor input provides an indication of attribute(s) of other objects, such as furniture items of the suite 100, luggage, etc. For example, the sensor input may provide an indication of the presence of luggage on the floor of the suite 100, or the position of a moveable item of furniture (e.g. a table or seat).

In examples described above, the output state helps control the environment of the suite 100. In other examples, the output state controllable is external to the suite 100. For example, the output state controllable may comprise a message or alert displayed outside of the suite 100, for example to be seen/heard by cabin crew.

In examples described above, the controller receives sensor input and uses the sensor input to determine one or more attributes of a passenger. In other examples, the one or more attributes of the passenger are received by the controller. For example, the sensor input received from the sensor equipment may itself comprise one or more passenger attributes. In such examples, the one or more passenger attributes may be determined by the sensor equipment and then sent to the controller. The controller uses the one or more passenger attributes to control the output state(s) of the suite. For example, a heart rate sensor may determine a value of a heart rate of the passenger, and send the determined value to the controller.

In examples where the sensor equipment comprises an image sensor, image analysis (e.g. involving performing object recognition on obtained image data) may be performed at the sensor equipment and/or at the controller.

In some examples, the logic condition input includes an aircraft state, the sensor equipment includes a thermal imaging equipment, a video equipment and/or a distance measurement equipment, and the output state includes a message/alert displayed within the suite and/or externally, for example to the cabin crew. If the aircraft state is "landed" and/or "deboarding" and the sensor input indicates that no passenger is present in the suite but that luggage has been left in the suite (e.g. in a stowage compartment), the output state may be controlled such that a message/alert is displayed. In some cases, a video feed from inside the stowage compartment is displayed to the exiting passenger and/or crew, to make the passenger and/or crew aware of the left luggage. The left luggage may be detected based on distance measurement data from the distance measurement equipment.

Where in the foregoing description, integers or elements are mentioned which have known, obvious or foreseeable equivalents, then such equivalents are herein incorporated as if individually set forth. Reference should be made to the claims for determining the true scope of the present invention, which should be construed so as to encompass any such equivalents. It will also be appreciated by the reader that integers or features of the invention that are described as preferable, advantageous, convenient or the like are optional and do not limit the scope of the independent claims. Moreover, it is to be understood that such optional integers or features, whilst of possible benefit in some embodiments of the invention, may not be desirable, and may therefore be absent, in other embodiments.

It should be noted that throughout this specification, "or" should be interpreted as "and/or".

The invention claimed is:

1. An aircraft passenger suite comprising an aircraft seat for use by a passenger, the aircraft passenger suite also comprising:
   a controller for controlling a number of output states of the aircraft passenger suite, the controller comprising a logic condition receiver operable to receive a logic condition input; and
   sensor equipment operable to provide a sensor input to the controller, the sensor input providing an indication of at least one attribute of a passenger of the aircraft passenger suite, the sensor equipment comprising one or more of: an image sensor, a pressure sensor and a physiological sensor,
   wherein the controller is configured to control at least one of the output states of the aircraft passenger suite, based on both the logic condition input and the sensor input, and
   wherein the sensor equipment comprises a plurality of image sensors, wherein each image sensor of the plurality of image sensors comprises or is comprised in a thermal imaging equipment arranged to obtain a thermal image of at least part of the aircraft passenger suite, and each image sensor of the plurality of image sensors being arranged in a different location in the aircraft passenger suite, wherein the controller is configured to obtain data representing a three-dimensional map of a volume within the aircraft passenger suite, the data generated using sensor input provided by the plurality of image sensors.

2. The aircraft passenger suite according to claim 1, wherein the output state controllable by the controller controls an environment within the aircraft passenger suite.

3. The aircraft passenger suite according to claim 1, wherein at least one of the plurality of image sensors comprises or is comprised in a video equipment.

4. The aircraft passenger suite according to claim 1, wherein the sensor equipment comprises a pressure sensor, wherein the pressure sensor is arranged under a support surface of the aircraft seat and/or a physiological sensor, wherein the physiological sensor comprises a heart rate sensor, a breathing rate sensor and/or a body temperature sensor.

5. The aircraft passenger suite according to claim 1, wherein the aircraft seat comprises a first seat part and a second seat part moveable with respect to the first seat part, the first seat part and the second seat part each comprising a respective support surface, wherein the sensor equipment comprises a first pressure sensor arranged under the support surface of the first seat part and a second pressure sensor arranged under the support surface of the second seat part.

6. The aircraft passenger suite according claim 1, wherein the at least one attribute of the passenger comprises one or more of: a breathing rate, a heart rate, and a body temperature, a posture, a comfort characteristic, a presence, a location, and/or a movement of the passenger.

7. The aircraft passenger suite according to claim 1, wherein the logic condition input includes:
an aircraft state, such as a status of the aircraft, such as: "boarding", "ready for take-off, taxi or landing (TTL)", "in flight", "experiencing turbulence", "landed" and/or "lifejacket inspection check;"
an aircraft cabin state, wherein the aircraft cabin state represents a status of the aircraft cabin, such as: "lights dimmed for night-time" and/or "meal time;"
an aircraft passenger suite state wherein the aircraft passenger suite state represents a status of the aircraft passenger suite, such as: "seat in bed configuration", "lights low/off", "furniture being deployed" and/or "furniture being stowed;" and/or
one or more preferences provided by the passenger such as an indication of passenger consent.

8. The aircraft passenger suite as claimed in claim 1, wherein the output state controllable by the controller includes at least one of a light level of the aircraft passenger suite, a temperature of the aircraft passenger suite or a part of the aircraft passenger suite, a message or warning displayed within the aircraft passenger suite, a message or warning displayed externally to the aircraft passenger suite and/or a deployment/stowage condition of a piece of furniture of the aircraft passenger suite, and/or providing an indication of whether or not medical assistance is required; and/or
controlling a display device of the aircraft passenger suite to aid passenger comfort.

9. The aircraft passenger suite according to claim 1, wherein the sensor equipment comprises an image sensor, wherein the logic condition input includes an aircraft state, and wherein the output state controllable is
a message display within the suite and/or a lighting level within the suite, such that, in use, if the sensor input indicates that a passenger has entered the suite, and the aircraft state is "boarding", then the controller controls the output state such that a welcoming message is displayed and/or welcome lighting is turned on or
a message/warning light within the suite and/or externally to a member of cabin crew, such that, in use, if the sensor input indicates that a passenger is not seated in the aircraft seat, and the aircraft state is "ready for taxi, take-off or landing", then the controller controls the output state such that the message/warning light is turned on.

10. The aircraft passenger suite according to claim 1, wherein the sensor equipment comprises an image sensor and/or a pressure sensor, wherein the logic condition input includes an aircraft cabin state and/or an aircraft suite state, and wherein the output state controllable is:
a lighting level within the suite, such that, in use, if the sensor input indicates that a passenger has got out of bed, and the aircraft cabin state is "lights dimmed for night-time" and/or the aircraft suite state is "low light level", then the controller controls the output state such that a light is turned on within the suite;
deployment/stowage of a meal table, such that, in use, if the sensor input indicates that a passenger is sitting in the seat, and the aircraft suite state is "deployment/stowage of the meal table" and/or the aircraft cabin state is "meal time", and the meal table is stowed, then the controller controls the output state such that the meal table is deployed; or
if the logic condition input includes an aircraft suite state the output state controllable optionally is deployment/stowage of a piece of furniture, such that, in use, if the sensor input indicates that a passenger or part of the passenger is in a path of deployment/stowage, and the aircraft suite state is "deployment/stowage of a piece of furniture", then the controller controls the output state such that deployment/stowage movement of the piece of furniture is ceased.

11. The aircraft passenger suite according to claim 1, wherein the sensor equipment comprises a physiological sensor, wherein the logic condition input includes one or more preferences provided by a passenger, and wherein the output state controllable is selected from the following:
providing an indication of whether or not medical assistance is required, such that, in use, if the sensor input indicates that a passenger requires medical assistance, and the one or more preferences indicate that the passenger has provided consent, then the controller controls the output state such that an indication that medical assistance is required is provided;
a lighting or cooling condition within the suite, such that, in use, if the sensor input indicates that a passenger is anxious, and the one or more preferences indicate that passenger has provided consent, then the controller controls the output state such that cooling and/or air circulation is turned on, suite lighting is adjusted, and/or a display device of the suite is controlled to aid passenger comfort; or
a heating or cooling condition within the suite, such as heating or cooling of the aircraft seat, such that, in use, if the sensor input indicates that a passenger is hotter or colder than expected, and the one or more preferences indicate that the passenger has provided consent, then the controller controls the output state such that heating, cooling, air circulation and/or air conditioning in the aircraft suite is turned on.

12. The aircraft passenger suite according to claim 1, wherein the sensor equipment comprises a breathing rate sensor, wherein the logic condition input includes an aircraft suite state such as a destination time zone and/or an estimated landing time and/or one or more preferences provided by a passenger, and wherein the output state controllable is a lighting level and/or noise cancellation within the suite, such that, in use, if the sensor input indicates that a passenger is asleep, and the aircraft suite state is "seat in bed configuration" and/or the one or more preferences indicate that the passenger has provided consent, then the controller controls the output state such that a lighting level, within the suite is adjusted, optionally based on a destination time zone and/or noise cancellation is turned on.

13. The aircraft passenger suite according to claim 1, wherein the sensor equipment further comprises a distance sensor for measuring a distance between a first location within the suite and a second location within the suite and providing a distance input to the controller, wherein, in use, the controller controls the at least one output state based on the distance input.

14. An aircraft passenger suite comprising:
an aircraft seat for use by a passenger; and
a controller for controlling a number of output states of the aircraft passenger suite, the controller comprising:
    a first receiver operable to receive a logic condition input; and
    a second receiver operable to receive image, pressure and/or physiological sensor data from sensor equipment, the sensor data representing a three-dimensional thermal map of a volume within the aircraft passenger suite and providing an indication of one or more attributes of a passenger of the aircraft passenger suite,
wherein the controller is configured to control at least one of the output states of the aircraft passenger suite based on both the logic condition input and the sensor data.

15. The aircraft passenger suite according to claim 14, wherein the controller is communicatively coupleable to a personal electronic device of the passenger, and wherein the controller is:
    configured to receive the sensor data from the personal electronic device and/or
    configured to receive the logic condition input from the personal electronic device.

16. An aircraft passenger suite comprising an aircraft seat for use by a passenger, the aircraft passenger suite also comprising:
    a controller for controlling a number of output states of the aircraft passenger suite, the controller comprising a logic condition receiver operable to receive a logic condition input, wherein the logic condition input optionally includes an indication of passenger consent; and
    sensor equipment said sensor equipment operable to provide a sensor input to the controller, the sensor input providing an indication of at least one attribute of a passenger of the aircraft passenger suite, and wherein the sensor equipment comprises a physiological sensor arranged to detect a physiological condition of the passenger, wherein the physiological sensor is a breathing rate sensor,
    wherein the controller is configured to control at least one of the output states of the aircraft passenger suite based on both the logic condition input and the sensor input, and
        controlling a display device of the aircraft passenger suite to aid passenger comfort by displaying a measured and/or desired breathing pattern to the passenger via the display device.

17. The aircraft passenger suite according to claim 16, wherein the output state controllable comprises providing an indication of whether or not medical assistance is required to a crew information panel.

* * * * *